US009206417B2

(12) United States Patent
Zahn et al.

(10) Patent No.: US 9,206,417 B2
(45) Date of Patent: Dec. 8, 2015

(54) MULTIPLEXED SEQUENTIAL LIGATION-BASED DETECTION OF GENETIC VARIANTS

(71) Applicant: Ariosa Diagnostics, Inc., San Jose, CA (US)

(72) Inventors: Jacob Zahn, San Jose, CA (US); Arnold Oliphant, San Jose, CA (US); Morassa Mohseni, San Jose, CA (US)

(73) Assignee: ARIOSA DIAGNOSTICS, INC., San Jose, CA (US)

( * ) Notice: Subject to any disclaimer, the term of this patent is extended or adjusted under 35 U.S.C. 154(b) by 308 days.

(21) Appl. No.: 13/946,392

(22) Filed: Jul. 19, 2013

(65) Prior Publication Data

US 2014/0024538 A1    Jan. 23, 2014

Related U.S. Application Data

(60) Provisional application No. 61/673,337, filed on Jul. 19, 2012, provisional application No. 61/708,334, filed on Oct. 1, 2012.

(51) Int. Cl.
| | | |
|---|---|---|
| *C12P 19/34* | (2006.01) | |
| *C12N 15/10* | (2006.01) | |
| *C12Q 1/68* | (2006.01) | |

(52) U.S. Cl.
CPC .......... *C12N 15/1072* (2013.01); *C12Q 1/6827* (2013.01)

(58) Field of Classification Search
USPC ................................. 435/6.12, 91.2
See application file for complete search history.

(56) References Cited

U.S. PATENT DOCUMENTS

| | | |
|---|---|---|
| 4,683,195 A | 7/1987 | Mullis et al. |
| 4,988,617 A | 1/1991 | Landegren et al. |
| 5,143,854 A | 9/1992 | Pirrung et al. |
| 5,242,794 A | 9/1993 | Whiteley et al. |
| 5,270,184 A | 12/1993 | Walker et al. |
| 5,399,491 A | 3/1995 | Kacian et al. |
| 5,409,818 A | 4/1995 | Davey et al. |
| 5,413,909 A | 5/1995 | Bassam et al. |
| 5,422,252 A | 6/1995 | Walker et al. |
| 5,437,975 A | 8/1995 | McClelland |
| 5,494,810 A | 2/1996 | Barany et al. |
| 5,547,839 A | 8/1996 | Dower et al. |
| 5,554,517 A | 9/1996 | Davey et al. |
| 5,578,832 A | 11/1996 | Trulson et al. |

(Continued)

FOREIGN PATENT DOCUMENTS

| | | |
|---|---|---|
| GB | 2299166 | 9/1996 |
| GB | 97044 | 3/1998 |

(Continued)

OTHER PUBLICATIONS

Search Report dated Aug. 12, 2014 for PCT/US2013/75683, entire document.

(Continued)

*Primary Examiner* — Kenneth Horlick
(74) *Attorney, Agent, or Firm* — Convergent Law Group LLP

(57) ABSTRACT

The present invention provides multiplexed sequential ligation-based analysis of genetic variants in a mixed sample, including copy number variations and single nucleotide polymorphisms. The invention employs the techniques of sequential ligation and amplification.

54 Claims, 3 Drawing Sheets

(56) References Cited

U.S. PATENT DOCUMENTS

| | | |
|---|---|---|
| 5,631,734 A | 5/1997 | Stern et al. |
| 5,648,245 A | 7/1997 | Fire et al. |
| 5,800,992 A | 9/1998 | Fodor et al. |
| 5,808,041 A | 9/1998 | Padhye et al. |
| 5,830,711 A | 11/1998 | Barany et al. |
| 5,834,758 A | 11/1998 | Trulson et al. |
| 5,856,092 A | 1/1999 | Dale et al. |
| 5,861,245 A | 1/1999 | McClelland et al. |
| 5,871,928 A | 2/1999 | Fodor et al. |
| 5,874,219 A | 2/1999 | Rava et al. |
| 5,876,924 A | 3/1999 | Zhang et al. |
| 5,888,740 A | 3/1999 | Han |
| 5,898,071 A | 4/1999 | Hawkins |
| 5,902,723 A | 5/1999 | Dower et al. |
| 5,936,324 A | 8/1999 | Montagu |
| 5,952,170 A | 9/1999 | Stroun et al. |
| 5,981,956 A | 11/1999 | Stern |
| 6,025,601 A | 2/2000 | Trulson et al. |
| 6,027,889 A | 2/2000 | Barany et al. |
| 6,045,996 A | 4/2000 | Cronin et al. |
| 6,054,564 A | 4/2000 | Barany et al. |
| 6,063,603 A | 5/2000 | Davey et al. |
| 6,090,555 A | 7/2000 | Fiekowsky et al. |
| 6,141,096 A | 10/2000 | Stern et al. |
| 6,156,504 A | 12/2000 | Gocke et al. |
| 6,185,030 B1 | 2/2001 | Overbeck |
| 6,201,639 B1 | 3/2001 | Overbeck |
| 6,210,891 B1 | 4/2001 | Nyren et al. |
| 6,218,803 B1 | 4/2001 | Montagu et al. |
| 6,225,625 B1 | 5/2001 | Pirrung et al. |
| 6,258,540 B1 | 7/2001 | Lo et al. |
| 6,268,148 B1 | 7/2001 | Barany et al. |
| 6,309,824 B1 | 10/2001 | Drmanac |
| 6,310,199 B1 | 10/2001 | Smith et al. |
| 6,312,892 B1 | 11/2001 | Barany et al. |
| 6,316,229 B1 | 11/2001 | Lizardi |
| 6,329,179 B1 | 12/2001 | Kopreski |
| 6,342,387 B1 | 1/2002 | Hayashizaki et al. |
| 6,386,749 B1 | 5/2002 | Watts et al. |
| 6,391,623 B1 | 5/2002 | Besemer et al. |
| 6,401,267 B1 | 6/2002 | Drmanac |
| 6,410,276 B1 | 6/2002 | Burg et al. |
| 6,506,594 B1 | 1/2003 | Barany et al. |
| 6,534,262 B1 | 3/2003 | McKernan et al. |
| 6,534,293 B1 | 3/2003 | Barany et al. |
| 6,562,573 B2 | 5/2003 | Halaka |
| 6,573,103 B1 | 6/2003 | Wald |
| 6,576,453 B2 | 6/2003 | Barany et al. |
| 6,797,470 B2 | 9/2004 | Barany et al. |
| 6,828,100 B1 | 12/2004 | Ronghi |
| 6,833,246 B2 | 12/2004 | Balasubramanian |
| 6,852,487 B1 | 2/2005 | Barany et al. |
| 6,858,412 B2 | 2/2005 | Willis et al. |
| 6,864,052 B1 | 3/2005 | Drmanac et al. |
| 6,911,345 B2 | 6/2005 | Quake et al. |
| 6,914,137 B2 | 7/2005 | Baker |
| 6,927,028 B2 | 8/2005 | Dennis et al. |
| 6,949,370 B1 | 9/2005 | Barany et al. |
| 6,977,162 B2 | 12/2005 | Dhallan |
| 7,014,994 B1 | 3/2006 | Barany et al. |
| 7,083,917 B2 | 8/2006 | Barany et al. |
| 7,097,980 B2 | 8/2006 | Barany et al. |
| 7,166,434 B2 | 1/2007 | Barany et al. |
| 7,198,894 B2 | 4/2007 | Barany et al. |
| 7,208,274 B2 | 4/2007 | Dhallan |
| 7,232,656 B2 | 6/2007 | Balasubramanian |
| 7,244,233 B2 | 7/2007 | Krantz et al. |
| 7,244,831 B2 | 7/2007 | Barany et al. |
| 7,312,039 B2 | 12/2007 | Barany et al. |
| 7,315,787 B2 | 1/2008 | Orlandi et al. |
| 7,320,865 B2 | 1/2008 | Barany et al. |
| 7,332,277 B2 | 2/2008 | Dhallan |
| 7,332,285 B2 | 2/2008 | Barany et al. |
| 7,343,190 B2 | 3/2008 | Krantz et al. |
| 7,358,048 B2 | 4/2008 | Barany et al. |
| 7,364,858 B2 | 4/2008 | Barany et al. |
| 7,429,453 B2 | 9/2008 | Barany et al. |
| 7,442,506 B2 | 10/2008 | Dhallan |
| 7,455,965 B2 | 11/2008 | Barany et al. |
| 7,459,311 B2 | 12/2008 | Nyren et al. |
| 7,527,929 B2 | 5/2009 | McKernan et al. |
| 7,556,924 B2 | 7/2009 | Barany et al. |
| 7,582,420 B2 | 9/2009 | Oliphant et al. |
| 7,598,060 B2 | 10/2009 | Dhallan |
| 7,601,491 B2 | 10/2009 | Collis et al. |
| 7,622,281 B2 | 11/2009 | Ronaghi et al. |
| 7,645,576 B2 | 1/2010 | Lo et al. |
| 7,648,824 B2 | 1/2010 | Nyren et al. |
| 7,700,323 B2 | 4/2010 | Willis et al. |
| 7,709,194 B2 | 5/2010 | Lo et al. |
| 7,709,201 B2 | 5/2010 | Barany et al. |
| 7,718,367 B2 | 5/2010 | Lo et al. |
| 7,718,370 B2 | 5/2010 | Dhallan |
| 7,727,720 B2 | 6/2010 | Dhallan |
| 7,727,727 B2 | 6/2010 | Collis |
| 7,754,428 B2 | 7/2010 | Lo et al. |
| 7,780,600 B2 | 8/2010 | Krantz et al. |
| 7,799,531 B2 | 9/2010 | Mitchell et al. |
| 7,807,431 B2 | 10/2010 | Barany et al. |
| 7,888,017 B2 | 2/2011 | Quake et al. |
| 7,901,884 B2 | 3/2011 | Lo et al. |
| 7,989,614 B2 | 8/2011 | Deggerdal et al. |
| 8,008,018 B2 | 8/2011 | Quake et al. |
| 8,195,415 B2 | 6/2012 | Fan et al. |
| 8,296,076 B2 | 10/2012 | Fan et al. |
| 8,318,430 B2 | 11/2012 | Chuu et al. |
| 2002/0045176 A1 | 4/2002 | Lo et al. |
| 2002/0132241 A1 | 9/2002 | Fan et al. |
| 2003/0003459 A1 | 1/2003 | Stahl |
| 2003/0044388 A1 | 3/2003 | Dennis et al. |
| 2003/0054386 A1 | 3/2003 | Antonarakis et al. |
| 2003/0064366 A1 | 4/2003 | Hardin et al. |
| 2003/0108913 A1 | 6/2003 | Schouten |
| 2003/0143599 A1 | 7/2003 | Makarov et al. |
| 2004/0009518 A1 | 1/2004 | Lo et al. |
| 2004/0101835 A1 | 5/2004 | Willis et al. |
| 2004/0203037 A1 | 10/2004 | Lo et al. |
| 2004/0214175 A9 | 10/2004 | McKernan et al. |
| 2005/0095618 A1 | 5/2005 | Tsuio et al. |
| 2005/0191656 A1 | 9/2005 | Drmanac et al. |
| 2006/0252068 A1 | 11/2006 | Lo et al. |
| 2006/0252071 A1 | 11/2006 | Lo et al. |
| 2006/0275789 A1 | 12/2006 | Willis et al. |
| 2007/0087345 A1 | 4/2007 | Olson-Munoz et al. |
| 2007/0172873 A1 | 7/2007 | Brenner et al. |
| 2007/0178478 A1 | 8/2007 | Dhallan |
| 2007/0207482 A1 | 9/2007 | Church et al. |
| 2007/0275402 A1 | 11/2007 | Lo et al. |
| 2008/0020390 A1 | 1/2008 | Mitchell et al. |
| 2008/0081338 A1 | 4/2008 | Lo et al. |
| 2008/0096766 A1 | 4/2008 | Lee |
| 2008/0138809 A1 | 6/2008 | Kapur et al. |
| 2008/0206748 A1 | 8/2008 | Olson et al. |
| 2008/0243398 A1 | 10/2008 | Rabinowitz |
| 2009/0018024 A1 | 1/2009 | Church et al. |
| 2009/0029377 A1 | 1/2009 | Lo et al. |
| 2009/0048124 A1 | 2/2009 | Leamon et al. |
| 2009/0061425 A1 | 3/2009 | Lo et al. |
| 2009/0087847 A1 | 4/2009 | Lo et al. |
| 2009/0099041 A1 | 4/2009 | Church et al. |
| 2009/0155776 A1 | 6/2009 | Lo et al. |
| 2010/0105049 A1 | 4/2010 | Ehrich et al. |
| 2010/0105052 A1 | 4/2010 | Drmanac et al. |
| 2010/0112575 A1 | 5/2010 | Fan et al. |
| 2010/0112590 A1 | 5/2010 | Lo et al. |
| 2010/0120076 A1 | 5/2010 | Braun et al. |
| 2010/0136529 A1 | 6/2010 | Shoemaker et al. |
| 2010/0184043 A1 | 7/2010 | Mitchell et al. |
| 2010/0184044 A1 | 7/2010 | Mitchell et al. |
| 2010/0184210 A1 | 7/2010 | Rossmanith et al. |
| 2010/0267034 A1 | 10/2010 | Lo et al. |
| 2010/0291571 A1 | 11/2010 | Stoughton et al. |
| 2010/0291572 A1 | 11/2010 | Stoughton et al. |
| 2011/0003293 A1 | 1/2011 | Stoughton et al. |

(56) References Cited

U.S. PATENT DOCUMENTS

| | | |
|---|---|---|
| 2011/0027771 A1 | 2/2011 | Deng |
| 2011/0039724 A1 | 2/2011 | Lo et al. |
| 2011/0059451 A1 | 3/2011 | Mitchell et al. |
| 2011/0086357 A1 | 4/2011 | Lo et al. |
| 2011/0105353 A1 | 5/2011 | Lo et al. |
| 2011/0117548 A1 | 5/2011 | Mitchell et al. |
| 2011/0124518 A1 | 5/2011 | Cantor |
| 2011/0143342 A1 | 6/2011 | Lo et al. |
| 2011/0151442 A1 | 6/2011 | Fan et al. |
| 2011/0171638 A1 | 7/2011 | Stoughton et al. |
| 2011/0172111 A1 | 7/2011 | Cantor |
| 2011/0177517 A1 | 7/2011 | Rava et al. |
| 2011/0178719 A1 | 7/2011 | Rabinowitz |
| 2011/0183330 A1 | 7/2011 | Lo et al. |
| 2011/0201507 A1 | 8/2011 | Rava et al. |
| 2011/0224087 A1 | 9/2011 | Quake et al. |
| 2011/0230358 A1 | 9/2011 | Rava et al. |
| 2011/0245085 A1 | 10/2011 | Rava et al. |
| 2011/0276277 A1 | 11/2011 | Lo et al. |
| 2011/0288780 A1 | 11/2011 | Rabinowitz |
| 2011/0312503 A1 | 12/2011 | Chuu |
| 2012/0003650 A1 | 1/2012 | Lo et al. |
| 2012/0010085 A1 | 1/2012 | Rava |
| 2012/0034603 A1 | 2/2012 | Oliphant et al. |
| 2012/0100548 A1 | 4/2012 | Rava et al. |
| 2012/0108460 A1 | 5/2012 | Quake et al. |
| 2012/0165203 A1 | 6/2012 | Quake et al. |
| 2012/0184449 A1 | 7/2012 | Hixson |
| 2012/0191358 A1 | 7/2012 | Oliphant et al. |
| 2012/0191367 A1 | 7/2012 | Stuelpnagel et al. |
| 2012/0219950 A1 | 8/2012 | Oliphant et al. |
| 2012/0225798 A1 | 9/2012 | Cantor et al. |
| 2012/0237928 A1 | 9/2012 | Rava et al. |
| 2012/0264115 A1 | 10/2012 | Rava |
| 2012/0264121 A1 | 10/2012 | Rava et al. |
| 2012/0270739 A1 | 10/2012 | Rava et al. |
| 2013/0029852 A1 | 1/2013 | Rava |
| 2014/0038181 A1* | 2/2014 | Lebedev et al. ............ 435/6.11 |

FOREIGN PATENT DOCUMENTS

| | | |
|---|---|---|
| WO | WO87/06270 | 10/1987 |
| WO | WO90/06995 | 6/1990 |
| WO | WO99/47964 | 9/1999 |
| WO | WO03/038120 | 5/2003 |
| WO | WO2007/100243 | 9/2007 |
| WO | WO2007/126377 | 11/2007 |
| WO | WO2008/118998 | 10/2008 |
| WO | WO2009/036525 | 3/2009 |
| WO | WO2009/102632 | 8/2009 |
| WO | WO2011/090556 | 7/2011 |
| WO | WO2011/090557 | 7/2011 |
| WO | WO2011/090558 | 7/2011 |

OTHER PUBLICATIONS

Search Report Received on Aug. 13, 2012 (PCT/US2011/046976), entire document.
Abadia-Molina, et al., "Immune phenotype and cytotoxic activity of lymploycytes from human term decidua against trophoblast", J. of Reproductive Immunology, n31:109-23 (1996).
Agostini, et al., "Circulating cell-free DNA: a promising marker of pathologic tumor response in rectal cancer patients receiving pre-operative chemotherapy", Ann. Surg. Oncol., 18(9):2461-68 (2011).
Alexandrov, et al., "Definition of a new alpha satellite suprachromosomal family characterized by monomeric organization", Nucleic Acids Research, 21(9):2209-15 (2003).
Anker, et al., "Spontaneous Release of DNA by Human Blood Lymphocytes as Shown in an in Vitro System", Cancer Research, 35:2375-82 (1975).
Anker, et al., "K-ras Mutations are found in DNA extreacted from the plasma of patients with colorectal cancer," Gastroenterology, 112:1114-20 (1997).
Anker, et al., Information carried by the DNA release by antigen-stimulated lymphocytes:, Immunology, 37:753-63 (1979).
Ashoor, et al., Fetal Fraction in Maternal Plasma Cell-Free DNA at 11-13 Weeks' Gestation: Effect of Maternal and Fetal Factors, Fetal Dian Ther DOI:10.1159/000337373 (Pub'd online May 4, 2012), entire document.
Ashoor, et al., "Chromosome-selective sequencing of maternal plasma cell-free DNA for first-trimester detection of trisomy 21 and trisomy 18", Am. J. of Obstet. Gynecol., (2012), doi: 10.1016/j.ajog.2012.01.029, entire document.
Arnheim, et al., "Molecular evidence for genetic exchanges among ribosomal genes on nonhomologous chromosomes in man and apes", PNAS USA, 77(12):7323-27 (1980).
Bandyopadhyay, et al, "Identification and characterization of satellite III subfamilies to the acrocentric chromosomes", Chromosome Research, 9:223-33 (2001).
Batzer and Deininger, "ALU Repeats and Human Genomic Diversity", Nature, 3:370-79 (2002).
Beard, "Embryological Aspects and Etiology of Carcinoma", The Lancet, Jun. 21, 1902, pp. 1758-1761.
Belokhvostov, et al., "Changes in the Fractional Composition of the Nucleic Acids in Blood Serum upon Rediation Damage Early Stage Abnormalities Following Gamma-Irradiation of Rats", Tsitologiia (Cytology) 1986, pp. 506-509.
Bianchi, "Prenatal diagnosis by analysis of fetal cells in maternal blood", J. of Pediatrics, 127(6):847-56 (1995).
Bianchi, "Isolation of fetal DNA from nucleated erythrocytes in maternal blood", PNAS USA, 87:3279-83 (1990).
Bianchi, "PCR Quantitation of Fetal Cells in Maternal Blood in Normal and Aneuploid Pregnancies", Am J. Hum. Genet., 61:822-29 (1997).
Biran, "On the Oncodevelopmental Rold of Human Imprinted Genes", 43:119-23 (1994).
Blaschke and Rappold, "The Pseudoautosomal regions, SHOX and disease", Curr. Opin. Gene. Dev., 16(3):23-29 (2006).
Bodurtha and Strauss, "Genomics and Prenatal Care", New Eng. J. of Medicine, 366:64-73 (2012).
Bombard, et al., "Fetal RHD genotype detection from circulating cell-free DNA in maternal plasma in non-sensitized RhD negative women", Prenat Diagn, 31:802-08 (2011).
Bradstock, et al., "Functional and phenotypic assessment of neonatal human leucocytes expressing natural killer cell-associated antigen", Immunology and Cell Biology, 71:535-42 (1993).
Camaschella, et al., "Prenatal Diagnosis of Fetal Hemoglobin Lepore—Boston Disease on Maternal Peripheral Blood", Blood, 75(11):2102-06 (1990).
Campbell, et al., "Subclonal phylogenetic structions in cancer revealed by ultra-deep sequencing", PNAS, 105(35):13081-86 (2008).
Cappuzzo, et al., "Epidermal growth factor receptor gene and protein and gefitinib sensitivity in non-small-cell lung cancer", J. Natl Cancer Inst., 97(9):643-55 (2005).
Cicuttini and Boyd, "Hemopoietic and Lymphoid Progenitro Cells in Human Umbilical Cord Blood", Developmental Immunology, 4:1-11 (1994).
Chen, et al., "Microsatellite alterations in plasma DNA of small cell lung cancer patients", Nature Medicine, 2(9):1033-35 (1996).
Chen, et al., "Noninvasive prenatal diagnosis of fetal trisomy 18 and trisomy 13 by maternal plasma DNA sequencing", PLos One, 6:e21791 (2011), entire document.
Chim, et al., "Detection of the placental epigenetic signature of the *maspin* gene in maternal plasma", PNAS USA, 102(41):14753-58 (2005).
Chiu, et al, "Effects of Blood-Processing Protocols on Fetal and Total DNA Quantification in Maternal Plasma", Clin. Chem., 47(9):1607-1613 (2001).
Chiu, et al., "Maternal plasma DNA analysis with massively parallel sequencing by ligation for noninvasive prenatal diagnosis of trisomy 21", 56:459-63 (2010).
Chiu, et al, "Noninvasive prenatal diagnosis of fetal chromosomal aneuploidy by massively parallel genomic sequencing of DNA in maternal plasma", PNAS USA 105:20458-63 (2008).

(56) References Cited

OTHER PUBLICATIONS

Chiu and Lo, "Non-invasive prenatal diagnosis by fetal nucleic acid analysis in maternal plasma: the coming of age", Semin. Fetal Neonatal Med., 16(2):88-93 (2011).

Chiu, et al., "Non-invasive prenatal assessment of trisomy 21 by multiplexed maternal plasma DNA sequencing: large scale validity study", Br Med J. 342:c7401 (2011), entire document.

Chiu, et al., "Noninvasive prenatal diagnosis of fetal chromosomal aneuploidy by massively parallel genomic sequencing of DNA in maternal plasma", PNAS USA 105:20458-63 (2008) Supporting Information.

Cirigiliano, et al., "Clinical application of multiplex quantitative fluorescent polymerase chain reaction QF-PCR for the repaid prenatal detection of common chromosome aneuploidies", Molecular Human Reproduction, 7(10):1001-06 (2001).

Cirigiliano, et al., "Rapid prenatal diagnosis of common chromosome aneuploidies by QF-PCR, results of 9 years of clinical experience", Prenatal diagnosis, 29:40-49 (2009).

Choo, et al., "A homologous subfamily of satellite III DNA on human chromosomes 14 and 22", Nucleic Acids Research, 18(19):5641-47 (1990).

Choo, et al., "A Chromosome 14-specific Human Satellite III DNA Subfamily That Shows Variable Presence on Different Chromosomes 14", Am J. Hum. Genet., 50:706-16 (1992).

Chromosome 14 map, Nature, 409:947-48 (2001).

Chu, et al., "A novel approach toward the challenge of accurately quantifying fetal DNA in maternal plasma", Prenat. Diag., 30:1226-29 (2010).

Ciccodicola, et al., "Differentially regulated and evolved genes in the fully sequences Xq/Yq pseudoautosomal region", Hum. Mol. Genet., 9(3):395-401 (2000).

Cockwell, et al., "Distribution of the D15A1 copy number polymorphism", European J. of Hum. Genet., 15:441-45 (2007).

Conover, Practical Nonparametric Statistics, pp. 295-301 (John Wiley & Sons, NY)(1971).

Costa, et al., "New strategy for prenatal diagnosis of X-linked disorders", N. Engl J. Med., 346:1502 (2002).

Datta, et al., "Sensitive Detection of Occult Breast Cancer by the Reverse-Transcriptase Polymerase Chain Reaction", J. of Clinical Oncology, 12(3): 475-82 (1994).

Dear, et al., "A High-Resolution Metric HAPPY Map of Human Chromosome 14" Genomics, 48:232-41 (1998).

Dennin, "DNA of Free and Complexed Origin in Human Plasma: Concentration and Length Distribution", Klin. Wochenschr., 57:451-56 (1979).

Dhallan, et al., "A non-invasive test for prenatal diagnosis based on fetal DNA present in maternal blood: a preliminary study", Lancet, 369(9560):474-81 (2007).

Dobrzycka, et al., "Circulating free DNA and p53 antibodies in plasma of patients with ovarian epithelial cancers", Annals of Oncology, 22:1133-40 (2011).

Dobrzycka, et al., "Prognostic significance of VEGF and its receptors in endometrioid endometrial cancer", Ginekol Pol. 81(6):422-25 (2010).

Office Action for U.S. Appl. No. 13/293,419, inventor A. Sparks, filed Nov. 10, 2011, entire document.

Final Office Action for U.S. Appl. No. 13/293,419, inventor A. Sparks, filed Nov. 10, 2011, entire document.

Advisory Action for U.S. Appl. No. 13/293,419, inventor A. Sparks, filed Nov. 10, 2011, entire document.

Office Action for U.S. Appl. No. 13/245,133, inventor A. Oliphant, filed Sep. 26, 2011, entire document.

Office Action for U.S. Appl. No. 13/316,154, inventor A. Oliphant, filed Dec. 9, 2011, entire document.

Office Action for U.S. Appl. No. 13/338,963, inventor A. Oliphant, filed Dec. 28, 2011, entire document.

Office Action for U.S. Appl. No. 13/689,417, inventor A. Oliphant, filed Nov. 29, 2012, entire document.

Duan, et al., "PstSNP-HapMap3: a database of SNPs with high population differentiation for HapMap3", Bioinformation, 3(3):139-41 (2008).

Earle, et al., "Identification of DNA Sequences Flanking the Breakpoin of Human t(14q21q) Robertsonian Translocations", Am J. Hum Genet., 50:717-24 (1992).

Ehrich, et al., "Noninvasive detection of fetal trisomy 21 by sequencing of fetal DNA in maternal blood: a study in a clinical setting", Am J. Obstet Gynecol, 2011:204:205 e1-11 (2011).

Fan, et al., "Noninvasive diagnosis of fetal aneuploidy by shotgun sequencing DNA from maternal blood", PNAS USA, 105(42):16266-71 (2008).

Fan, et al., "Analysis of the Size Distributions of Fetal and Maternal Cell-Free DNA by Paired-End Sequencing", Clin. Chem., 56(8):1279-80 (2010).

Fan, et al., "Sensitivity of noninvasive prenatal detection of fetal aneuploidy from maternal plasma using shotgun sequencing is limited only by counting statistics", PLoS One, 5:e10439 (2010), entire document.

Fejgin, et al., "Fetal cells in the uterine cervix: a source for early non-invasive prenatal diagnosis", Prenat. Diag., 21:619-21 (2001).

Finning, et al., "Effect of high throughput RHD typing of fetal DNA in maternal plasma on use of anti-RhD immunoglobulin in RhD negative pregnant women: prospective feasibility study", Br Med J., 336:816-18 (2008).

Fisher, et al., "Genetic evidence that placental site trophoblastic tumours can originate from a hydatidiform mole or a normal conceptus", Br. J. Cancer, 65:355-58 (1992).

Fournie, et al., "Plasma DNA as Cell Death Marker in Elderly Patients", Gerontology, 39:215-221 (1993).

Fowke, Genetic analysis of human DNA recovered from minute amounts of serum and plasma, J. of Immunol. Meth., 180:45-51 (1995).

Geifman-Holzman, et al., "Fetal RhD genotyping in fetal cells flow sorted from maternal blood", Am. J. Obstet. Gynecol., 174(3):818-22 (1996).

Ghossein, et al., "Detection of Circulating Tumor Cells in Patients With Localized and Metastatic Prostatic Carcinoma Clinical Implications", J. of Clin. Oncology, 13(5):1995-200 (1995).

Gold, "Cancer and Pregnancy: Parallels in Growth, Invasion, and Immune Modulation and Implicationsa for Cancer Therapeutic Agents", Mayo Clin. Proc., 84(11):985-1000 (2009).

Gosden, et al., "Satellite DNA Sequences in the Human Acrocentric Chromosomes: Information from Translocations and Heteromorphisms", Am. J. Hum. Genet., 33:243-51 (1981).

Greeley, et al., "Get ready for the flood of fetal gene screening", Nature, 469:289-91 (2011).

Green, et al., "Gestational Trophoblastic Disease: A Spectrum of Radiologic Diagnosis", Radiographics, 16(6):1371-84 (1996).

Gribben, et al., "Detection of Residual Lymphoma Cells by Polymerase Chain Reaction in Peripheral Blood is Significantly Less Predictive for Relapse Than Detection in Bone Marrow", Blood, 83(12):3800-07 (1994).

Guatelli, et al., "Isothermal, in vitro amplification of nucleic acids by a multienzyme reaction modeled after retroviral replication", PNAS USA, 87(5):1874-78 (1990).

Han, et al, "Molecular Chytogenetic Characterization of 17 rob(13q14q) Robertsonian Translocations by FISH, Narrowing the Region Containing the Breakpoints", Am J. Hum. Genet., 55:960-67 (1994).

Hardingham, et al., "Detection of Circulating Tumor Cells in Colorectal Cancer by Immunogead-PCR is a Sensitive Prognostic marker for Relapse of Disease", Molecular Medicine, 1(7):789-94 (1995).

Harrell, Regression modeling strategies, §§9.2.2 and 1.10.5 (Springer Vertag)(2001).

Heid, et al., "Real Time Quantitative PCR", Genome Res., 6:986-94 (1996).

Heilig, et al., "The DNA sequence and analysis of human chromosome 14", Nature, 421:601-09 (2003).

Ho, et al., "Activation Status of T and NK Cells in the Endometrium Throughout Menstrual Cycle and Normal and Abnormal Early Pregnancy", Human Immunology, 49:130-36 (1996).

(56) References Cited

OTHER PUBLICATIONS

Hoon, et al., "Detection of Occult Melanoma Cells in Blood With a Multiple-Marker Polymerase Chain Reaction Assay", J. of Clinical Oncology, 13(8):2109-116 (1995).
Hosny, et al., "TP53 mutations in circulating fee DNA from Egyptian patients with non-Hodgkin's lymphoma", Cancer Lett., 275(2):234-39 (2009).
International Human Genome Sequencing Consortium, "Initial sequencing and analysis of the human genome", Nature, 409:860-921 (2001).
Irizarry, et al., "Summaries of Affymetrix GeneChip probe level data", Nuc. Acid Res., 31(4):e5 (2003), entire document.
Kamnasaran and Cox, "Current status of chromosome 14", J. Med. Genet., 39:81-90 (2002).
Kazakov, et al., "Extracellular DNA in the Blood of Pregnant Women", Tsitologiia (Cytology), 37(3):232-37 (1995).
Kogan, et al., "An improved method for prenatal diagnosis of genetic diseases by analysis of amplified DNA sequences", New England J. of Medicine, 317(6):985-90 (1987).
Krebs, et al., "The Unitarian or Trophoblastic Thesis of Cancer" Medical Record, 163:149-74 (Jul. 1950).
Landegren, et al., "A ligase-mediated gene detection technique", Science, 241:1077 (1988).
Leon, "Free DNA in the Serum of Cancer Patients and the Effect of Therapy", Cancer Res., 37:646-50 (1977).
Li, et al., "A photocleavable fluorescent nucleotide for DNA sequencing and analysis", PNAS USA, 100(2):414-19 (2003).
Liao, et al., "Targeted massively parallel sequencing of maternal plasma DNA permits efficient and unbiased detection of fetal alleles", Clin Che, 57:92-101 (2011).
Lo, et al., "Detection of single-copy fetal DNA sequence from maternal blood", The Lancet, 335:1463-64 (1990).
Lo, et al., "Two-way cell traffic between mother and fetus: biological and clinical implications", Blood, 88:4390-95 (1996).
Lo, et al., "Presence of fetal DNA in maternal plasma and serum", The Lancet, 350:485-86 (1997).
Lo, et al., "Quantitative analysis of fetal DNA in maternal plasma and serum: implications for noninvasive prenatal diagnosis", Am J. Hum. Genetics, 62:768-75 (1998).
Lo, et al., "Prenatal diagnosis of fetal RhD status by molecular analysis of maternal plasma", N Engl J Med, 339:1734-38 (1998).
Lo, et al., "Rapid clearance of fetal DNA from maternal plasma", Am J. Hum. Genetics, 64:218-24 (1999).
Lo, et al., "Digital PCR for the molecular detection of fetal chromosomal aneuploidy", PNAS USA, 104:13116-21 (2007).
Lo, et al., "Plasma placental RNA allelic ratio permits noninvasive prenatal chromosomal aneuploidy detection", Nat. Med., 13:218-23 (2007).
Lo, et al., Maternal plasma DNA sequencing reveals the genome-wide genetic and mutational profile of the fetus. Sci Transl Med, 2:61ra91 (2010), entire document.
Lo, "Fetal nucleic acids in maternal blood: the promises", Clin. Chem. Lab Med., 50(5):xxx-xxx (DOI 10.1515/CCLM.2011.765) (2011).
Lun, et al., "Microfluidics Digital PCR Reveals a Higher than Expected Fraction of Fetal DNA in Maternal Plasma", Clin. Chem., 54(10):1664-72 (2008).
Lun, et al., "Noninvasive prenatal diagnosis of monogenic diseases by digital size selection and relative mutation dosage on DNA in maternal plasma", PNAS USA, 105(50):19920-25 (2008).
Makrigiorgos, et al., "A PCR-based amplification method retaining the quantitative difference between two complex genomes", Nat. Biotech., 20:936-39 (2002).
Sparks, et al., "Selective analysis of cell-free DNA in maternal blood for evaluation of fetal trisomy", Prenatal Diagnosis, 32:1-7 (2012).
Sparks, et al., "Non-invasive Prenatal Detection and Selective Analysis of Cell-free DNA Obtained from Maternal Blood: Evaluation for Trisomy 21 and Trisomy 18", Am. J. Obstet. Gynecol., (2012), doi:10.1016/j.ajog.2012.01.030, entire document.
Stroun, et al., "Neoplastic Characteristics of the DNA Found in the Plasma of Cancer Patients", Oncology, 46: 318-322 (1989).
Stroun, et al., "Isolation and Characterization of DNA from the Plasma of Cancer Patients", Eur. J. Cancer Clin. Oncol., 23(6) 707-12 (1987).
Stroun, et al., "Circulating Nulceic Acids in Higher Organisms", Rev. Cytol. 51:1-48 (1977).
Stroun, et al., The Origin and Mechanism of Circulating DNA, Annals New York Academy of Sciences, 906:161-68 (2000).
Sullivan, et al., "Evidence for Structural Heterogeneity from Molecular Cytogenetic Analysis of Dicentric Robertsonian Translocations", Am. J. Hum. Genet., 59:167-75 (1996).
Tagle, et al., "An optimized Alu-PCR primer pair for human-specific amplification of YACs and somatic cells hybrids", Human Molecular Genetics, 1(2):121-22 (1992).
Tomilin, et al., "Mechanisms of Chromosome Destabilization in Human Cells", Sov. Sci. Rev. D. Physiochem. Biol., 10:39-89 (1992).
Tong, et al., "Noninvasive prenatal detection of fetal trisomy 18 by epigenetic allelic ratio analysis in maternal plasma: theoretical and empirical considerations", Clin Chem, 52:2194-202 (2006).
Tsui, et al., "Systematic microarray-based identification of placental mRNA in maternal plasma: towards non-invasive prenatal gene expression profiling", J. Med Genet, 41:461-67 (2004).
Tsui, et al., "Noninvasive prenatal diagnosis of hemophilia by microfluidics digital PCR analysis of maternal plasma DNA", Blood, 117:3684-91 (2011).
Ulbright, "Germ cell tumors of the gonads: a selective review emphasizing problems in differential diagnosis, newly appreciated, and controversial issues," Modern Pathology, 18:S61-S79 (2005).
Vasioukhin, et al., "Point mutations in the N-ras gene in the blood plasma DNA of patients with myelodysplastic cyndrome or acute myelogenous leukaemia", British J. of Haematology, 86:774-79 (1994).
Vogelstein, et al., "Digital PCR", PNAS USA, 96:9236-41 (1999).
Wachtel, et al., "Fetal cells in the maternal circulation: Isolation by multiparameter flow cytometry and confirmation by polymerase chain reaction", Human Reprod., 6(10):1466-69 (1991).
Wald, et al., "Maternal serum screening for Down's syndrome in early pregnancy", BMJ, 297:883-87 (1988).
Wald, et al., "Antenatal maternal serum screening for Down's syndrome: results of a demonstration project", BMJ, 305(6850):391-94 (1992).
Walker, et al., "Human DNA quantitation using Alu element-based polymerase chain reaction", Analytical Biochem., 315:122-28 (2003).
Wang, et al., "PennCNV: An integrated hidden Markov model designed for high-resolution copy number variation detection in whole-genome SNP genotyping data", Genome Res., 17:1665-74 (2007).
Ward, et al., "Reactivities of serotyping monoclonal antibodies with culture-adapted human rotaviruses", J. Clin. Microbiol. 29(3):422-25 (1991).
Winsor, et al., "Maternal Cell Contamination in Uncultured Amniotic Fluid", Prenatal Diagnosis, 16:49-54 (1996).
Witt, et al., "An improved, non-isotopic method of screening cells from patients with abnormalities of sexual differentiation for Y chromosomal DNA content", J. Med. Genet., 30:304-07 (1993).
Wu and Wallace, "The ligation amplification reaction (LAR)—Amplification of specific DNA sequences using sequential rounds of template-dependent ligation", Genomics, 4:560-69 (1989).
Young and Davis, "Efficient isolation of genes by using antibody probes", PNAS 80:1194-98 (1983).
Enders, et al., "Fetal morbidity and mortality after acute human parvovirus B19 infection in pregnancy: prospective evaluation of 1018 cases", Prenatal Diagnosis, 24:513-18 (2004).
Smith, et al., "Quantitative phenotyping via deep barcode sequencing", Genome Res., 19:1836-42 (2009).
Van Opstal, et al., "Rapdi aneuploidy detection with multiplex ligation-dependent probe amplification: a prospective study of 4000 amniotice fluid samples", Eur. J. of Hum. Genetics, 17:112-21 (2009).

(56) References Cited

OTHER PUBLICATIONS

Xie and Tammi, "CNV-seq, a new method to detect copy number variation using high throughput sequencing", BMC Bioinformatics, 10:80 (2008), doi 10.1186/1471-2105-10-80, p. 1-9.
Search Report Received on Oct. 15, 2012 (PCT/US2011/046981), entire document.
Search Report Received on Jan. 20, 2012 (PCT/US2012/21955), entire document.
Search Report Received on May 2, 2012 PCT/US2011/046935), entire document.
Search Report Received on May 10, 2012 (PCT/US2012/026754), entire document.
Search Report Received on May 11, 2012 (PCT/US2012/022261), entire document.
Search Report Received on Feb. 21, 2013 (PCT/US2011/046963), entire document.
Search Report Received on Apr. 19, 2013 (PCT/US2012/70177), entire document.
Office Action for U.S. Appl. No. 13/356,133, inventor A. Oliphant, filed Jan. 23, 2012, entire document.
Office Action for U.S. Appl. No. 13/356,575, inventor A. Oliphant, filed Jan. 23, 2012, entire document.
Office Action for U.S. Appl. No. 13/689,206, inventor A. Oliphant, filed Nov. 39, 2012, entire document.
Final Office Action for U.S. Appl. No. 13/689,206, inventor A. Oliphant, filed Nov. 39, 2012, entire document.
Office Action for U.S. Appl. No. 13/013,732, inventor A. Oliphant, filed Jun. 25, 2011, entire document.
Office Action for U.S. Appl. No. 13/013,732, inventor A. Oliphant, filed Jun. 25, 2011), entire document.
Office Action for U.S. Appl. No. 13/407,978, inventor K. Song, filed Feb. 29, 2012, entire document.
Office Action for U.S. Appl. No. 13/205,490, inventor A. Sparks, filed Aug. 8, 2011, entire document.
Office Action for U.S. Appl. No. 13/687,169, inventor A. Sparks, filed Nov. 28, 2012, entire document.
Office Action for U.S. Appl. No. 13/205,570, inventor A. Sparks, filed Aug. 8, 2011, entire document.
Office Action for U.S. Appl. No. 13/687,025, inventor A. Sparks, filed Nov. 28, 2012, entire document.
Bianchi, et al., "Large Amounts of Cell-free DNAS Are Present in Amniotic Fluid", Clin. Chem., 47(10) 1867-69 (2001).
Centre for Genomics Education, "Changes to Chromosome Structure—Translocations", The Australasian Genetics Resource Book, ,www.genetics.com, pp. 1-5 (2007).
Chiu, et al., "Non-invasive prenatal diagnosis by single molecule counting technologies", Trends in Genomics, 25(7):324-31 (2009).
Hayden, et al., "Multiplex-Ready PCR: A new method for multiplexed SSR and SNP genotyping", BMC Genomics, 9:80:1-12 (2007).
Hsuih, et al., "Novel, ligation-depdent PCR assay for detection of hepatitis C in serum", J. of Clin. Microbiology, 34(3):501-07 (1996).
Huang, et al., "Identification of a family of alternatively splied mRNA species of angiopoietin-1", Blood, 95:1993-99 (2000).
Indolfi, et al., "Perinatal Transmission of Hepatitis C Virus Infection", J. Med. Virol., 81:836-43 (2009).
Mardis, et al., "The impact of next-generation sequencing technology on genetics", Trends in Genetics, 24(3):133-41 (2007).
Porreca, et al., "Multiplex amplification of large sets of human exons", Nat. Methods, 4(11):931-36 (2007).
Schouten, et al., "Relative quantification of 40 nucleic acid sequences by multiplex ligation-dependent probe amplification", Nuc. Ac. Res., 30(12):e57 (2002).
Tewhey, et al., "Microdroplet-based PCR enrichment for large-scale targeted sequencing", Nat. Biotech., 27(11):1025-31 (2009).
Zolotukhina, et al., "Analysis of Cell-free DNA in Plasma and Serum of Pregnant Women", J. of Hist. and Cytochem., 53:297-99 (2005).
Office Action for U.S. Appl. No. 13/356,575, filed Jan. 23, 2012, inventor Oliphant, entire document.
Office Action for U.S. Appl. No. 13/689,206, filed Nov. 29, 2012, inventor Oliphant, entire document.
Office Action for U.S. Appl. No. 13/356,133, filed Jan. 23, 2012, inventor Oliphant, entire document.
Office Action for U.S. Appl. No. 13/013,732, filed Jun. 25, 2011, inventor Oliphant, entire document.
Office Action for U.S. Appl. No. 13/405,839, filed Feb. 27, 2012, inventor Oliphant, entire document.
Office Action for U.S. Appl. No. 13/407,978, filed Feb. 29, 2012, inventor Song, entire document.
Office Action for U.S. Appl. No. 13/605,505, filed Sep. 6, 2012, inventor Struble, entire document.
Office Action for U.S. Appl. No. 13/687,169, filed Nov. 28, 2012, inventor Sparks, entire document.
Office Action for U.S. Appl. No. 13/687,169, filed Nov. 28, 2012, inventor Sparks , entire document.
Office Action for U.S. Appl. No. 13/205,490, filed Aug. 8, 2011, inventor Sparks, entire document.
Office Action for U.S. Appl. No. 13/687,025, filed Nov. 28, 2012, inventor Sparks, entire document.
Office Action for U.S. Appl. No. 13/687,025, filed Nov. 28, 2011, inventor Sparks, entire document.
Office Action for U.S. Appl. No. 13/205,570, filed Aug. 8, 2011, inventor Sparks, entire document.
Office Action for U.S. Appl. No. 13/293,419, filed Nov. 10, 2011, Sparks, entire document.
Office Action for U.S. Appl. No. 13/205,603, filed Aug. 8, 2011, inventor Sparks, entire document.
Office Action for U.S. Appl. No. 13/274,309, filed Oct. 15, 2011, inventor Struble, entire document.
Office Action for U.S. Appl. No. 13/245,133, filed Sep. 26, 2011, inventor Oliphant, entire document.
Office Action for U.S. Appl. No. 13/689,417, filed Nov. 29, 2012, inventor Oliphant, entire document.
Office Action, filed Dec. 9, 2011, inventor Oliphant for U.S. Appl. No. 13/316,154, entire document.
Australian Patent Examination Report No. 1 dated Feb. 20, 2014 for 2011285512, entire document.
Australian Patent Examination Report No. 1 dated Mar. 4, 2014 for 2011285518, entire document.
Australian Patent Examination Report No. 1 dated Feb. 7, 2014 for 2011285477, entire document.
EPO Examination Report dated Nov. 21, 2013 for App. No. 11745880.2, entire document.
EPO Examination Report dated Nov. 21, 2013 for App. No. 11745881.1, entire document.
EPO Examination Report dated Nov. 28, 2013 for App. No. 11745883.6, entire document.
Search Report dated Sep. 12, 2013 for PCT/US 2012/026754, entire document.
Search Report dated Nov. 15, 2013 for PCT/US 2013/51310, entire document.
Search Report dated May 14, 2013 for PCT/US 2014/17092, entire document.
Mangs, Curr. Genomics, "The Human Pseudoautosomal Region (PAR): Origin, Function and Future", 8(2):129-36 (2007).
Mansfield, "Diagnosis of Down syndrome and other aneuploidies using quantitative polymerase chain reaction and small tandem repeat polymorphisms", Human Molecular Genetics, 2(1):43-50 (1993).
Mantzaris, et al., "Preliminary report: correct diagnosis of sex in fetal cells isolated from cervical mucus during early pregnancy", ANZJOG, 45(6):529-32 (2005).
Margulies, et al., "Genome sequencing in microfabricated high-density picolitre reactors", Nature, 437(15):376-80 and errata (2005).
Mikhaylov, et al., "Changes in the quantity and synthesis of DNA in the nuclei of large decidual cells of rats in the course of their differentiation", Tsitologiia (Cytology),41(6):677-83 (1992).
Mikhaylov, et al., "Synthesis and content of DNA in human decidual cells at various stages of differentiation according to flow cytometry analysis", Tsitologiia (Cytology), 34(6):67-72 (1992).
Moffet-King, et al., "Natural Killer Cells and Pregnancy", Nature Reviews Immunology, 2002(2):656-63.

(56) References Cited

OTHER PUBLICATIONS

Moreno and Gomella, "Circulating Prostate Cancer Cells Detected by Reverse Transcription-Polymerase Chain Reaction (RT-PCR: What do they mean?", Cancer Control Journal, 5(6):1-5 (1998).
Mulcahy, et al., "Plasma DNA K-rase Mutations in Patients with Gastrointestinal Malignancies," Annals New York Academy of Sciences, 25-28 (2006).
Mujezinovic and Alfirevic, Obstet. Gynecol., "Procedure-Related Complications of Amniocentesis and Chorionic Villous Sampling: A Systematic Review", 110(3):687-94 (2007).
Mueller, et al., "Isolation of fetal trophoblast cells from peripheral blood of pregnant women", The Lancet, 336:197-200 (1990).
Nawroz, et al., "Microsatellite alterations in serum DNA of head and neck cancer patients", Nature Medicine, 2(9):1035-37 (1996).
Nelson, et al., "Alu polymerase chain reaction: A method for rapid isolation of human-specific sequence from complex DNA sources," PNAS USA, 86:6686-90 (1989).
Ng, et al., "mRNA of placental origin is readily detectable in maternal plasma", PNAS USA, 100:4748-53 (2003).
Oei, et al., "Clusters of regulatory signals for RNA polymerase II transcription associated with Alu family repeats and CpG islands in human promoters", Genomics, 83:873-82 (2004).
Page, et al., "Breakpoint diversity illustrates distinct mechanisms for Robertsonian translocation formation", Hum. Molec. Genet., 5(9):1279-88 (1996).
Page, et al., Br. J. Cancer, "Detection of HER2 amplification in circulating free DNA in patients with breast cancer", 104(8):1342-48 (2011).
Paolella, et al., "The Alu family repeat promoter has a tRNA-like bipartite structure", EMBO J., 2(5):691-96 (1983).
Papageorgiou, et al., "DNA methylation ratio permits noninvasive prenatal diagnosis of trisomy 21", Nat. Med., 17:510-13 (2011).
Petersen, et al., "Down Syndrome Due to De Novo Robertsonian Translocation t(14q21q): DNA Polymorphism Analysis Suggests that the Origin of the Extra q21 is Maternal", Am. Ju. Hum. Genet. 49:529-36 (1991).
Poon, et al., "Differential DNA methylation between fetus and mother as a strategy for detecting fetal DNA in maternal plasma", Clin Chem, 48:35-41 (2002).
Rijinders, et al., "Fetal sex determination from maternal plasma in pregnancies at risk for congenital adrenal hyperplasia", Obstet Gynecol, 98:374-78 (2001).
Ro, et al., "Association of Polymorphisms of Interleukin-8, CXCR1, CXCR2, and Selectin With Allograft Outcomes in Kidney Transplantation", Transplantation, 91(1):57-64 (2011).
Robbins, et al., *Pathologic Basis of Disease 5th Ed.*, Chapter 23, pp. 1071-1088 (1994).
Ronaghi, et al., "A Sequencing Method Based on Real Time Pyrophosphate", Science, 281:363-65 (1998).
Ross, et al., "The DNA sequence of the human X Chromosome", Nature 434:325-37 (2005).
Roth, et al., Molec. Oncol., "Screening for circulating nucleic acids and caspase activity in the peripheral blood as potential diagnostic tools in lung cancer", 5(3):281-91 (2011).
Royston, "An extension of Shapiro and Wilk's W test for normality to large samples", Applied Statistics, 31:115-24 (1982).
Royston, "Model-based screening by risk with application to Down's syndrome", Statistics in Medicine, 11(2)257-68 (1992).
St. Clair, "Copy Number Variation and Schizophrenia", Schizophr. Bull., 35(1):9-12 (2009).
Saiki, et al., "Primer-directed Enzymatic Amplification of DNA with a Thermostable DNA Polymerase", Science, 239:487-91 (1987).
Savas, "Useful genetic variation databases for oncologists investigating the genetic basis of variable treatment response and survival in cancer", Acta Oncol., 49(8):1217-26 (2010).
Shendure, et al., "Accurate Multiplex Polony Sequencing of an Evolved Bacterial Genome", Science, 309:1728-32 (2005).
Schallhammer, et al., "Phenotypic comparison of natural killer cells from peripheral blood and from early pregnancy decidua", Early Pregnancy: Biology and Medicine, 3:15-22 (1997).
Schroder, et al., "Transplacental passage of blood cells", J. of Medical Genetics, 12:230-42 (1974).
Schuster, et al, "Next-generation sequencing transforms today's biology", Nat. Methods, 5:16-18 (2008).
Scriven, et al., "Robertsonian translocations—reproductive reisks and indications for preimplantation genetic diagnosis", Human Reproduction, 16(11):2267-73 (2001).
Sebat, et al., "Strong Association of De Novo Copy Number Mutations with Autism", Science, 316(5823):445-49 (2007).
Sehnert, et al., "Optimal detection of fetal chromosomal abnormalities by massively parallel DNA sequencing of cell-free fetal DNA from maternal blood", Clin Chem, 57: 1042-49 (2011).
Shamash, et al., "Preimplantation genetic haplotyping a new application for diagnosis of translocation carrier's embryo—preliminary observations of two robertsonian translocation carrier families", J. Assist. Reprod. Genet., 28:77-83 (2011).
Shapiro, et al., "Determination of Circulating DNA Levels in Patients with Benign or Malignant Gastrointestinal Disease", Cancer, 51:2116-20 (1983).
Simpson and Elias, "Isolating Fetal Cells from Maternal Blood", JAMA, 270(19):2357-61 (1993).
Simpson, et al., "Isolating Fetal Cells in Maternal Circulation for Prenatal Diagnosis", Prenatal Diagnosis, 14:1229-42 (1994).
Simpson, "Is Cell-Free Fetal DNA from Maternal Blood Finally Ready for Prime Time?", Obst & Gynecol., 119(5):1-3 (2012).
Snyder, et al., "Universal noninvasive detection of solid organ transplant rejection", PNAS USA, 108(5):6229-34 (2011).
Sorenson, "Cancer Epidemiology, Biomarkers and Prevention", Cancer Epidem. Biomarkers Prev., 3__67-71 (1994).
Smith, et al., "Detection of melanoma cells in peripheral blood by means of reverse transcriptase and polymerase chain reaction", The Lancet, 338:1227-29 (1991).
Smith, et al.. "Placental apoptosis in normal human pregnancy", Am. J. Obstet. Gynecol, Jul. 1997, pp. 57-65.
Sorenson, et al., "Soluble normal and mutated DNA sequences from single-copy genes in human blood", Cancer Epidemmiol. Biomarkers, 3:64-71 (1994).
Sparks, et al., "Noninvasive prenatal detection and selective analysis of cell-free DNA obtained from maternal blood: evaluation for trisomy 21 and trisomy 18", Am. J. Obstet. Gynecol., (2012), 206:319.e1-9.

\* cited by examiner

MULTIPLEXED SEQUENTIAL LIGATION-BASED DETECTION OF GENETIC VARIANTS

RELATED APPLICATIONS

This application claims priority to U.S. Ser. No. 61/673,337, filed Jul. 19, 2012 and 61/708,334, filed Oct. 1, 2012.

FIELD OF THE INVENTION

This invention relates to methods for multiplexed sequential ligation-based analysis of nucleic acid regions of interest.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Genetic abnormalities account for a wide number of pathologies, including syndromes caused by chromosomal aneuploidy (e.g., Down syndrome) and those caused by germline mutations resulting in either monogenic or polygenic diseases or disorders. Diagnostic methods for determining genetic anomalies have become standard techniques for identifying specific syndromes, diseases and disorders. In particular, prenatal diagnostics have become standard practice in high-risk populations to determine the presence or absence of certain disorders. Detection of both gross chromosomal abnormalities, such as trisomies, translocations and large insertions or deletions, and single gene traits, such as single gene mutations or polymorphisms associated with Rh blood group status, autosomal dominant or X-linked disorders, or autosomal recessive disorders are useful in detecting actual and potential pathologies and disorders that may affect a fetus. For example, chromosomal abnormalities such as trisomies 13, 18, and 21, the Robertsonian translocations associated with certain forms of Down syndrome and other syndromes, and larger deletions such as those found on chromosome 22 in DiGeorge syndrome all impact significantly on fetal health.

Similarly, detection of single gene disorders in a fetus, e.g., mutations in genes causing Tay-Sachs disease, sickle cell anemia, and thalassemia or copy number variants in diseases such as spinal muscular atrophy (SMA), may help parents to make important decisions regarding the health and care of the child. In addition, genetic status associated with blood group system status provides important information for maternal and/or and fetal health, and in many instances such knowledge provides an opportunity for intervention to prevent any deleterious outcomes in the pregnancy or immediately following birth.

Although conventional technology provides detection methods for these different genetic abnormalities, currently different techniques are required to interrogate different classes of mutations. Conventional methods of prenatal diagnostic testing for chromosomal aneuploidy currently requires removal of a sample of fetal cells directly from the uterus for genetic analysis, using either chorionic villus sampling (CVS) between 11 and 14 weeks gestation or amniocentesis after 15 weeks. However, these invasive procedures carry a risk of miscarriage of around one percent (see Mujezinovic and Alfirevic, Obstet. Gynecol., 110:687-694 (2011)). Current analysis of fetal cells typically involves karyotyping or fluorescent in situ hybridization (FISH) and does not provide information about single gene traits; thus, additional tests are required for identification of single gene diseases and disorders. Therefore, a mother desiring genetic information on the status of her fetus must undergo multiple tests to test for various genetic abnormalities.

Methods providing accurate quantification of non-polymorphic factors such as genetic copy number variations with simultaneous identification of genetic polymorphisms or mutations in a maternal sample would be a powerful tool to identify, e.g., potential medical complications in a mother and her fetus. Alternatively or in addition, the methods of the invention can be applied to mixed samples such as those comprising host/pathogen or host/transplant nucleic acids. The present invention addresses this need.

SUMMARY OF THE INVENTION

This Summary is provided to introduce a selection of concepts in simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides improved methods and systems for multiplexed sequential ligation-based analysis of genetic variations. The methods of the invention allow for amplification of regions of interest from chromosomes and/or reference chromosomes to detect chromosomal abnormalities such as aneuploidies, large insertions or deletions, and polymorphisms from the same or different regions of interest. Alternatively or in addition, the methods of the invention can be applied to mixed samples such as those comprising host/pathogen or host/transplant nucleic acids. The methods of the invention utilize sequential hybridization, elongation (optional), ligation and amplification reactions of an initial set of oligonucleotide probes and of at least one subsequent set of oligonucleotide probes in the same locus or region of interest. Using these methods in a sequential manner with two sets of oligonucleotide probes allows for increased fidelity and confidence in the accuracy of the genetic information obtained from each region of interest.

In some embodiments, the invention provides a method for identifying a genomic region of interest from a single source in a sample comprising DNA from two different sources, comprising the steps of: providing a sample comprising DNA from two different sources; introducing to the sample a first set of oligonucleotide probes comprising a first fixed sequence oligonucleotide complementary to a 3' region in a genomic region of interest and a second fixed sequence oligonucleotide complementary to a 5' region in the genomic region of interest; hybridizing the first set of oligonucleotide probes to the genomic region of interest in the sample; ligating the hybridized oligonucleotides of the first set of oligonucleotide probes to create first ligation products complementary to the genomic region of interest; introducing to the first ligation products a second set of oligonucleotide probes comprising a first fixed sequence oligonucleotide complementary to a 3' region in the first ligation product and a second fixed sequence oligonucleotide complementary to a 5' region in the first ligation product; hybridizing the second set of oligonucleotide probes to the first ligation products; ligating the hybridized oligonucleotides of the second set of oligonucleotide probes to create second ligation products complementary to the first ligation products; amplifying the second ligation products to create amplification products; and analyzing the amplification products, wherein the analysis of the amplification products identifies the genomic region of interest from the single source in the sample.

In some aspects of this embodiment, the first set of oligonucleotide probes further comprises one or more bridging oligonucleotides that hybridize to the genomic region of interest between and adjacent to the first and second fixed sequence oligonucleotides of the first set of oligonucleotide probes, and in the same or other aspects, the second set further comprises one or more bridging oligonucleotides that hybridize to the first ligation products between and adjacent to the first and second fixed sequence oligonucleotides of the second set of oligonucleotide probes.

In other aspects of this embodiment, the oligonucleotides of the first set of oligonucleotide probes and/or the second set of oligonucleotide probes are complementary to non-adjacent regions in the genomic region of interest, and the region between the first fixed sequence oligonucleotide and the second fixed sequence oligonucleotide of the first and/or second set is extended with a polymerase and dNTPs to create contiguously complementary oligonucleotides. In an alternative aspect, the fixed sequence oligonucleotides of the first set and/or second set of oligonucleotide probes are complementary to adjacent regions in the genomic region of interest.

In some aspects of this embodiment, at least one fixed sequence oligonucleotide of the second set of oligonucleotide probes comprises a complementary region that overlaps a ligation junction of the first ligation products, and in other aspects, both the first and second fixed sequence oligonucleotides of the second set of oligonucleotide probes comprise a complementary region that overlaps with a ligation junction of the first ligation products. In yet other aspects, at least one fixed sequence oligonucleotide of the second set of oligonucleotide probes comprises the region of a fixed sequence oligonucleotide of the first set of oligonucleotide probes that is complementary to the genomic region of interest, and in other aspects, both fixed sequence oligonucleotides of the second set of oligonucleotide probes comprise a region of the fixed sequence oligonucleotides that is complementary to the genomic region of interest.

Other embodiments of the invention provide a method for identifying a genomic region of interest from a single source in a sample comprising DNA from two different sources, comprising the steps of: providing a sample comprising DNA from two different sources; introducing to the sample a first set of oligonucleotide probes comprising a first fixed sequence oligonucleotide complementary to a 3' region in a genomic region of interest, a second fixed sequence oligonucleotide complementary to a 5' region in the genomic region of interest, and one or more bridging oligonucleotides that hybridize to the genomic region of interest between and adjacent to the first and second fixed sequence oligonucleotides of the first set of oligonucleotide probes; hybridizing the first set of oligonucleotide probes to the genomic region of interest in the sample; ligating the hybridized oligonucleotides of the first set of oligonucleotide probes to create first ligation products complementary to the genomic region of interest; introducing to the first ligation products a second set of oligonucleotide probes comprising a first fixed sequence oligonucleotide complementary to a 3' region in the first ligation product, a second fixed sequence oligonucleotide complementary to a 5' region in the first ligation product, and one or more bridging oligonucleotides that hybridize to the first ligation product between and adjacent to the first and second fixed sequence oligonucleotides of the second set of oligonucleotide probes; hybridizing the second set of oligonucleotide probes to the first ligation products; ligating the hybridized oligonucleotides of the second set to create second ligation products complementary to the first ligation products; amplifying the second ligation products to create amplification products; and analyzing the amplification products, wherein analysis of the amplification products identifies the genomic region of interest from the single source in the sample.

Yet other embodiments of the invention provide a method for identifying a genomic region of interest from a single source in a sample comprising DNA from two different sources, comprising the steps of: providing a sample comprising DNA from two different sources; introducing to the sample a first set of oligonucleotide probes comprising a first fixed sequence oligonucleotide complementary to a 3' region in a genomic region of interest and a second fixed sequence oligonucleotide complementary to a 5' region in the genomic region of interest, wherein the first and second fixed sequence oligonucleotides are complementary to non-adjacent regions in the genomic region of interest; hybridizing the first set of oligonucleotide probes to the genomic region of interest in the sample; extending the region between the first fixed sequence oligonucleotide and the second fixed sequence oligonucleotide of the first set of oligonucleotide probes with a polymerase and dNTPs to create contiguously hybridized oligonucleotides of the first set of oligonucleotide probes complementary to the genomic region of interest; ligating the contiguously hybridized oligonucleotides of the first set to of oligonucleotide probes create first ligation products complementary to the genomic region of interest; introducing to the first ligation products a second set of oligonucleotide probes comprising a first fixed sequence oligonucleotide complementary to a 3' region in the first ligation product and a second fixed sequence oligonucleotide complementary to a 5' region in the first ligation product, wherein the first and second fixed sequence oligonucleotides are complementary to non-adjacent regions in the first ligation product; hybridizing the second set of oligonucleotide probes to the first ligation products; extending the region between the first fixed sequence oligonucleotide and the second fixed sequence oligonucleotide of the second set with a polymerase and dNTPs to create contiguously hybridized oligonucleotides of the second set of oligonucleotide probes complementary to the first ligation product; ligating the contiguously hybridized oligonucleotides of the second set of oligonucleotide probes to create second ligation products complementary to the first ligation products; amplifying the second ligation products to create amplification products; and analyzing the amplification products, wherein the analysis of the amplification products identifies the genomic region of interest from the single source in the sample.

Yet other embodiments provide a method for identifying genetic variations in one or more genomic regions of interest, comprising the steps of: providing a nucleic acid comprising at least one region of interest from a sample that comprises nucleic acids from two or more sources; introducing at least one initial set of oligonucleotide probes comprising a first fixed sequence oligonucleotide probe that anneals 5' in the region of interest, a second fixed sequence nucleotide probe that anneals 3' in the region of interest and a bridging oligonucleotide probe that anneals between the first and second fixed oligonucleotide probes; extending the first fixed sequence oligonucleotide probe if it does not hybridize contiguously to the bridging oligonucleotide probe; extending the bridging oligonucleotide probe if it does not hybridize contiguously to the second fixed oligonucleotide probe; ligating the hybridized oligonucleotide probes from the initial set of oligonucleotide probes to create first ligation products complementary to the region of interest; introducing at least one subsequent set of oligonucleotide probes comprising a first fixed sequence oligonucleotide probe that anneals 5' in the first ligation products, a second fixed sequence nucleotide probe that anneals 3' in the first ligation products and a bridging oligonucleotide probe that anneals between the first and second fixed oligonucleotide probes in the first ligation products; extending the first fixed sequence oligonucleotide probe of the subsequent set of oligonucleotide probes if it does not hybridize contiguously to the bridging oligonucleotide probe of the subsequent set of oligonucleotide probes; extending the bridging oligonucleotide probe of the subsequent set of oligonucleotide probes if it does not hybridize contiguously to the second fixed oligonucleotide probe of the subsequent set of oligonucleotide probes; ligating the hybridized oligonucleotide probes from the second set of oligonucleotide probes to create second ligation products complementary to the first ligation products; amplifying the second ligation products; and analyzing the amplification products, wherein the analysis of the amplification products identifies the genetic variations in one or more regions of interest. In some aspects, the bridging oligonucleotide of the initial set of oligonucleotide probes hybridizes immediately contiguous to and between the between the first and second fixed oligonucleotide probes of the initial set of oligonucleotide probes, and in some aspects, one or both of the first fixed sequence oligonucleotide and the bridging oliogonucleotide of the initial set of oligonucleotide probes is extended following hybridization using dNTPs and a DNA polymerase to provide contiguously hybridized fixed and bridging oligonucleotide probes in the initial set of oligonucleotide probes. In some aspects, the bridging oligonucleotide of the subsequent set of oligonucleotide probes hybridizes immediately contiguous to and between the between the first and second fixed oligonucleotide probes of the subsequent set of oligonucleotide probes, and in some aspects, one or both of the first fixed sequence oligonucleotide and the bridging oliogonucleotide of the subsequent set of oligonucleotide probes is extended following hybridization using dNTPs and a DNA polymerase to provide contiguously hybridized fixed and bridging oligonucleotide probes in the subsequent set of oligonucleotide probes.

In yet other embodiments, the invention provides a method for identifying genetic variants in one or more genomic regions of interest, comprising the steps of: providing DNA comprising the at least one region of interest from a sample that comprises DNA from two or more sources; introducing at least one initial set of oligonucleotide probes comprising a first fixed sequence oligonucleotide probe that anneals 5' in the region of interest, a second fixed sequence nucleotide probe that anneals 3' in the region of interest; extending the region between the first fixed sequence oligonucleotide probe and the second fixed sequence oligonucleotide probe of the initial set if they do not hybridize contiguously with a polymerase and dNTPs to create continguously hybridized oligonucleotide probes from the initial set; ligating the contiguously hybridized oligonucleotide probes from the initial set of oligonucleotide probes to create first ligation products complementary to the region of interest, with a ligation junction corresponding to the site of ligation between the first fixed sequence oligonucleotide probe from the initial set; introducing at least one subsequent set of oligonucleotide probes comprising a first fixed sequence oligonucleotide probe that anneals 5' in the first ligation products, a second fixed sequence nucleotide probe that anneals 3' in the first ligation products wherein the first and second fixed sequence nucleotide probes are separated by one or more bases; extending the region between the first fixed sequence oligonucleotide probe and the second fixed sequence oligonucleotide probe of the subsequent set if they do not hybridize contiguously with a polymerase and dNTPs to create contiguously hybridized oligonucleotide subsequent probes; ligating the contiguously hybridized subsequent oligonucleotide probes to create second ligation products complementary to the first ligation products with a second ligation junction corresponding to the site of ligation between the first fixed sequence oligonucleotide probe and the second fixed sequence oligonucleotide probe of the subsequent set of oligonucleotide probes, wherein the first and second ligation junctions are different relative to one another in the second ligation products; amplifying the second ligation products; and analyzing the amplification products, wherein the analysis of the amplification products will identify genetic variants in one or more genomic regions of interest. In some aspects, the ligation junctions of the initial set of oligonucleotide probes and the subsequent set of oligonucleotide probes are the same, and in some aspects they are different.

In some aspects of these embodiments, the methods of the invention further comprise a step of amplifying the first ligation products after the first ligating step and before the second introducing step, where in some aspects, the amplification is linear, and in others the amplification is exponential.

In most aspects of these embodiments, the method is multiplexed; that is, performed on two or more genomic regions of interest from the single source, including at least 24, 48, 92, 180, 360, 500 or more genomic regions of interest from the single source.

In some aspects of these embodiments, the subsequent or second ligation products are amplified by linear amplification methods, and in other aspects, the subsequent or second ligation products are amplified by exponential amplification methods.

In some aspects of these embodiments, the fixed sequence oligonucleotides of one or more sets of oligonucleotide probes are unimolecular probes. In some aspects, the first and second fixed sequence oligonucleotide probes of one or both of the initial and subsequent sets of oligonucleotides probes are linked together in one molecule as precircle probes.

These and other aspects, features and advantages will be provided in more detail as described herein.

In some aspects, the first and second fixed sequence oligonucleotide probes of one or both of the initial and subsequent sets of oligonucleotides probes are linked together in one molecule as precircle probes.

These and other aspects, features and advantages will be provided in more detail as described herein.

DETAILED DESCRIPTION OF THE INVENTION

Figure 1A:
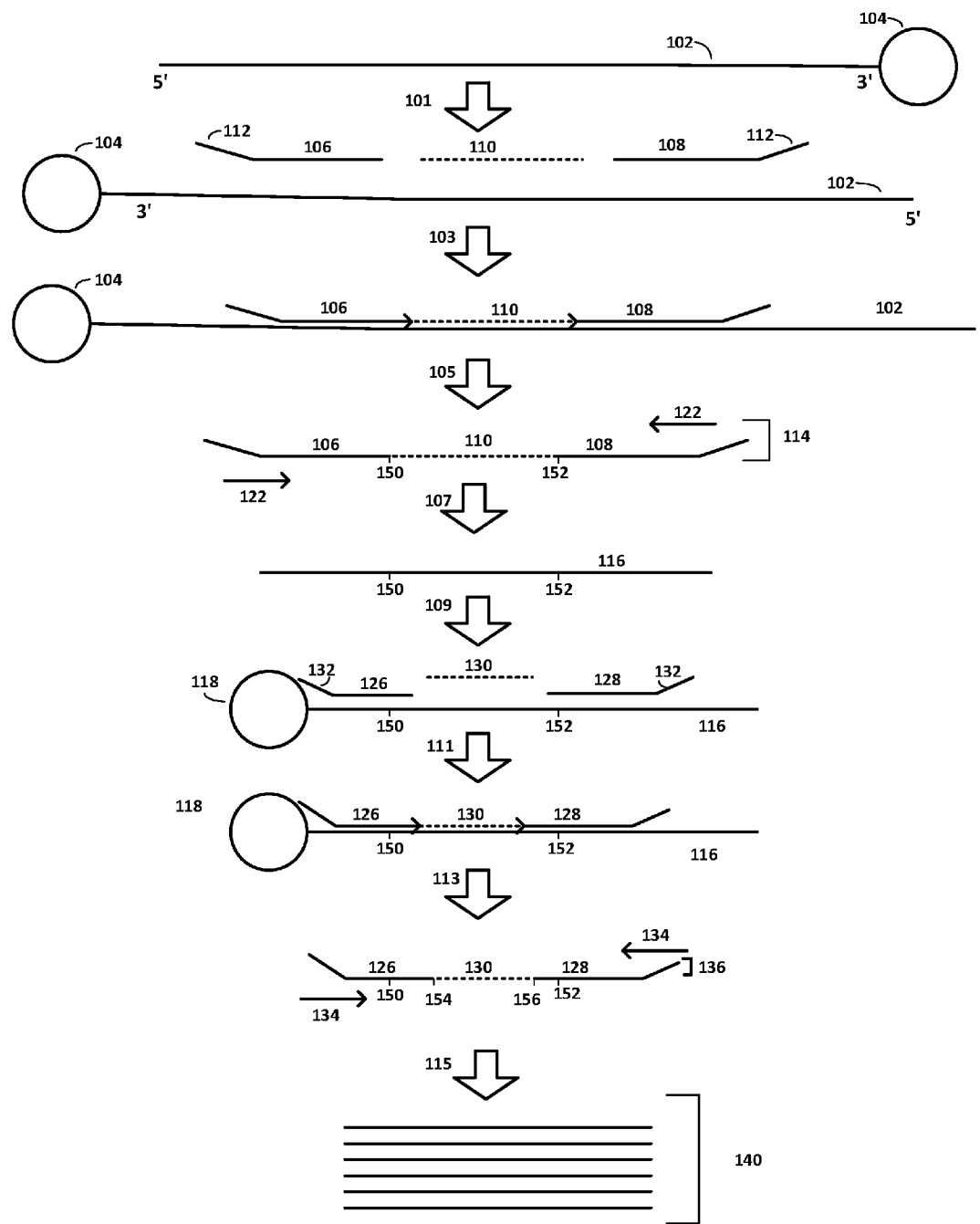
FIG. 1A is a simplified schematic of one embodiment of the multiplexed sequential ligation-based analysis methods of the present invention.

The methods described herein may employ, unless otherwise indicated, conventional techniques and descriptions of molecular biology (including recombinant techniques), cell biology, biochemistry, and microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, et al., Eds., *Genetic Variation: A Laboratory Manual* (2007); Dieffenbach, Dveksler, Eds., *PCR Primers: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, L., *Biochemistry* (4th Ed.) W.H. Freeman, New York (1995); Gait, "*Oligonucleotide Synthesis: A Practical Approach*" IRL Press, London (1984); Nelson and Cox, *Lehninger, Principles of Biochemistry*, $3^{rd}$ Ed., W. H. Freeman Pub., New York (2000); and Berg et al., *Biochemistry*, $5^{th}$ Ed., W.H. Freeman Pub., New York (2002), all of which are herein incorporated by reference in their entirety for all purposes. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by the appended claims.

It should be noted that as used herein and in the appended claims, the singular forms "a," "an," and "the" include plural referents unless the context clearly dictates otherwise. Thus, for example, reference to "a nucleic acid region" refers to one, more than one, or mixtures of such regions, and reference to "a method" includes reference to equivalent steps and methods known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those limits are also included in the invention.

All publications mentioned herein are incorporated by reference for all purposes including the purpose of describing and disclosing formulations and methodologies that that might be used in connection with the presently described invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention.

Definitions

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "amplified nucleic acid" is any nucleic acid molecule whose amount has been increased more than ten-fold by any nucleic acid amplification or replication method performed in vitro as compared to its starting amount.

The term "copy number variation" or "CNV" as used interchangeably herein are alterations of the DNA of a genome that results in a cell having an abnormal number of copies of one or more loci in the DNA. CNVs that are clinically relevant can be limited to a single gene or include a contiguous set of genes. A CNV can also correspond to relatively large regions of the genome that have been deleted, inverted or duplicated on certain chromosomes, up to and including one or more additional copies of a complete chromosome. The term CNV as used herein does not refer to any sequence-related information, but rather to quantity or "counts" of genetic regions present in a sample.

The term "diagnostic tool" as used herein refers to any composition or method of the invention used in, for example, a system in order to carry out a diagnostic test or assay on a patient sample.

The term "enrichment" means any method performed in vitro that increases the level of a nucleic acid molecule at least two-fold as compared to its starting amount.

The term "L2 amplification" refers to any amplification technique that utilizes two or more ligation events in the initial or subsequent, rounds of hybridization-ligation-amplification cycles to a nucleic acid region of interest. Such amplification techniques include those taught in U.S. Ser. No. 13/013,732, filed Jan. 25, 2011; Ser. No. 13/245,133, filed Sep. 26, 2011; Ser. No. 13/205,570, filed Aug. 8, 2011; Ser. 13/293,419, filed Nov. 10, 2011; Ser. No. 13/205,409, filed Aug. 8, 2011; Ser. No. 13/205,603, filed Aug. 8, 2011; Ser. No. 13/407,978, filed Feb. 29, 2012; Ser. No. 13/274,309, filed Oct. 15, 2011; Ser. No. 13/316,154, filed Dec. 9, 2011, and Ser. No. 13/338,963, filed Dec. 28, 2011, all of which are incorporated herein in their entirety.

The term "hybridization" or "anneal" generally means the reaction by which the pairing of complementary strands of nucleic acid occurs. DNA is usually double-stranded, and when the strands are separated they will re-hybridize under the appropriate conditions. Hybrids can form between DNA-DNA, DNA-RNA or RNA-RNA. They can form between a short strand and a long strand containing a region complementary to the short one. Imperfect hybrids can also form, but the more imperfect they are, the less stable they will be (and the less likely to form).

The terms "locus" and "loci" as used herein refer to a nucleic acid region of known location in a genome.

The terms "oligonucleotides" or "oligos" as used herein refer to linear oligomers of natural or modified nucleic acid monomers, including deoxyribonucleotides, ribonucleotides, anomeric forms thereof, peptide nucleic acid monomers (PNAs), locked nucleotide acid monomers (LNA), and the like, or a combination thereof, capable of specifically binding to a single-stranded polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g., 8-12, to several tens of monomeric units, e.g., 100-200 or more.

As used herein the term "polymerase" refers to an enzyme that links individual nucleotides together into a long strand, using another strand as a template. There are two general types of polymerase—DNA polymerases, which synthesize DNA, and RNA polymerases, which synthesize RNA. Within these two classes, there are numerous sub-types of polymerases, depending on what type of nucleic acid can function as template and what type of nucleic acid is formed.

As used herein "polymerase chain reaction" or "PCR" refers to a technique for replicating a specific piece of target DNA in vitro, even in the presence of excess non-specific DNA. Primers are added to the target DNA, where the primers initiate the copying of the target DNA using nucleotides and, typically, Taq polymerase or the like. By cycling the temperature, the target DNA is repetitively denatured and copied. A single copy of the target DNA, even if mixed in with other, random DNA, can be amplified to obtain several to many to billions of copies or replicates. The polymerase chain reaction can be used to detect and measure very small amounts of DNA and to create customized pieces of DNA. In some instances, linear enrichment methods may be used as an alternative to PCR.

The term "polymorphism" as used herein refers to any genetic changes in a locus that may be indicative of that particular loci, including but not limited to single nucleotide polymorphisms (SNPs), methylation differences, short tandem repeats (STRs), and the like.

Generally, a "primer" is an oligonucleotide used to, e.g., prime DNA extension, ligation and/or synthesis, such as in the synthesis step of the polymerase chain reaction or in the primer extension techniques used in certain sequencing reactions. Generally, a "probe" is used in hybridization techniques, is complementary to a region of interest and is used to detect a region of interest.

The term "research tool" as used herein refers to any method of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "selected nucleic acid region" or "selected sequence" or "region of interest" as used herein refers to a nucleic acid region corresponding to a locus in a nucleic acid from a sample that is to be interrogated. Regions of interest may be located on the same chromosomes or on one or more different chromosomes.

The terms "selective amplification" and "selectively amplify" and the like refer to an amplification procedure that depends in whole or in part on hybridization of an oligonucleotide primer to a sequence in a region of interest or a selected sequence.

The terms "sequencing" and "sequence determination" and the like as used herein refer generally to any and all biochemical methods that may be used to determine the order of nucleotide bases in a nucleic acid.

The terms "specifically binds" and "specific binding" and the like as used herein, when referring to a binding partner (e.g., a nucleic acid primer or probe, antibody, etc.) results in the generation of a statistically significant positive signal under the designated assay conditions. Typically the interaction will subsequently result in a detectable signal that is at least twice the standard deviation of any signal generated as a result of undesired interactions (background).

The term "universal" when used to describe an amplification procedure refers to the use of a single primer or set of primers for a plurality of amplification reactions. For example, in the detection of 96 different target sequences, all the templates may share identical universal priming sequences, allowing for the multiplex amplification of the 96 different sequences using a single set of primers. The use of such primers greatly simplifies multiplexing in that only two primers are needed to amplify a plurality of selected nucleic acid sequences. The term "universal" when used to describe a priming site is a site to which a universal primer will hybridize. It should also be noted that "sets" of universal priming sequences/primers may be used. For example, in highly multiplexed reactions, it may be useful to use several sets of universal sequences, rather than a single set; for example, 96 different nucleic acids may have a first set of universal priming sequences, and the second 96 nucleic acids may have a different set of universal priming sequences, etc.

The Invention in General

The present invention provides improved methods and systems for multiplexed sequential ligation-based analysis of genetic variations. The methods of the invention allow for amplification of regions of interest from chromosomes and/or reference chromosomes for detection of chromosomal abnormalities such as aneuploidies, copy number variations, large and small insertions or deletions, rearrangements, single nucleotide polymorphisms (SNPs), and differences in short tandem repeats (STRs) from the same or different regions of interest in a mixed sample (e.g., a maternal/fetal sample). Alternatively or in addition, the methods of the invention can be applied to mixed samples such as those comprising host/pathogen or host/transplant nucleic acids. The multiplexed sequential ligation-based analysis methods are applicable to diagnostics and diagnostic tools, and are applicable to research tools as well.

The methods of the invention utilize sequential hybridization, elongation (optional), ligation and amplification reactions of an initial set of oligonucleotide probes and of at least one subsequent set of oligonucleotide probes in the same locus or region of interest. Using these methods in a sequential manner with two sets of oligonucleotide probes allows for increased fidelity and confidence in the accuracy of the genetic information obtained from each region of interest.

In short, an initial (first) set of oligonucleotide probes—in some embodiments comprising a first fixed sequence probe, a second fixed sequence probe and a bridging probe—is allowed to hybridize to a region of interest. This initial set of oligonucleotide probes is then elongated, if necessary, and ligated; the first ligation product is then, optionally, amplified. These steps of the methods of the invention utilizing the initial set of oligonucleotide probes correspond to the L2 amplification method. However, building on the L2 method, after ligation of the initial set of oligonucleotide probes and an optional amplification step, a subsequent (second) set of oligonucleotide probes—also in some embodiments comprising a first fixed sequence probe, a second fixed sequence probe and a bridging probe—is then added to the first ligation product (or, optionally a first amplification product of the first ligation product). The subsequent set of oligonucleotide probes and is allowed to hybridize to the first ligation or amplification product, is elongated (if necessary), and then the oligonucleotide probes from the subsequent set of oligonucleotides are ligated to one another. The second ligation product of the subsequent set of oligonucleotide probes is, preferably, amplified, and these second amplification products are then sequenced. In aspects where the first and second fixed sequence probes do not hybridize contiguously to one another, the first fixed sequence probe can be extended using dNTPs and a polymerase until the first and second fixed sequence probes are hybridized contiguously to one another, where they can be ligated and amplified Typically more than one set of initial (first) and subsequent (second) oligonucleotide probes are used; that is, in most embodiments at least first and second sets of initial oligonucleotide probes are used (i.e., multiplexing), where the first and second initial oligonucleotide sets hybridize to different regions of interest (e.g., different loci) in the nucleic acid sample. The first and second subsequent oligonucleotide sets hybridize to the same regions of interest as the corresponding first and second initial sets of initial oligonucleotides, but to different regions of interest from one another. That is, more than one region of interest is interrogated, each region of interest is different, and the steps are performed with an initial set and a subsequent set of oligonucleotide probes for each region of interest. In practice the methods of the invention may be multiplexed to interrogate 10 regions of interest or more, 12 regions of interest or more, or 24, 28, 60, 96, 128, 200, 400, 500, 1000, 2500, or 5000 regions of interest or more from a sample.

In other embodiments, the initial and/or subsequent set of oligonucleotide probes comprise first and second fixed sequence probes with no bridging oligonucleotide probe. In aspects where the first and second fixed sequence probes hybridize contiguously to one another, the first and second fixed sequence probes can be ligated and then amplified, etc. In aspects where the first and second fixed sequence probes do not hybridize contiguously to one another, the first fixed sequence probe can be extended using dNTPs and a polymerase until the first and second fixed sequence probes are hybridized contiguously to one another, where they can be ligated and amplified.

A distinct advantage of the invention is that the regions of interest can be analyzed using a variety of detection and quantification techniques, including but not limited to hybridization techniques, digital PCR and high throughput sequencing.

Sequential Analysis of Selected Regions of Interest

FIG. 1A is a simplified schematic of one embodiment of the multiplexed sequential ligation-based genomic analysis methods of the present invention. The embodiment exemplified in FIG. 1A shows sequential analysis of a single region of interest. FIG. 1A shows method 100, where a nucleic acid 102 comprising a region of interest that is optionally immobilized to a solid support 104. Such immobilization of nucleic acid 102 and of other nucleic acids in subsequent steps is in fact not used in preferred embodiments. At step 101, an initial set of oligonucleotide probes is added to the nucleic acid 102. The initial set of oligonucleotide probes in this embodiment consists of a first fixed sequence probe 106, a second fixed sequence probe 108 and a bridging oligonucleotide probe 110. First 106 and second 108 fixed sequence probes each comprise universal priming sequence 112. Universal priming sequence 112 comprises a sequence to allow for universal amplification in a later step and may comprise other sequences useful for manipulating, identifying and/or quantifying the amplification product as described infra. It should be noted that the universal priming sequences 112 associated with the first fixed sequence probe 106 and the second fixed sequence probe 108 may be the same, or, in some embodiments, may be different. If such universal priming sequences 112 are different, in preferred embodiments the melting temperature ($T_m$) of the primers used in any subsequent amplification hybridized to the universal priming sequences are preferably similar.

In the embodiment shown in FIG. 1A, the fixed sequence oligonucleotide probes and the bridging oligonucleotide probes of a set are shown as being allowed to anneal simultaneously; however, in alternative embodiments, the bridging oligonucleotide probes may instead be added to the annealing reaction after the fixed sequence oligonucleotide probes have annealed, optionally following the removal of unhybridized fixed sequence oligonucleotide probes.

At step 103, the initial set of oligonucleotide probes is allowed to anneal to the region of interest in nucleic acid 102, where the first fixed sequence oligonucleotide 106 in the initial set anneals 5' in the region of interest, the second fixed sequence oligonucleotide 108 in the initial set anneals 3' in the region of interest, and the bridging oligonucleotide 110 in the initial set anneals between the first and second fixed sequence oligonucleotides in the region of interest. The arrows on the ends of the first fixed sequence oligonucleotide probe and the bridging oligonucleotide probe indicate that these oligonucleotide probes may be extended by a polymerase and dNTPs if the first and second fixed and the bridging oligonucleotide of the initial set do not anneal completely contiguous to one another in the region of interest. In specific embodiments, however, the bringing oligo will anneal immediately adjacent to both the 5' and 3' fixed oligonucleotides.

At step 105, ligation product 114 comprising first fixed sequence probe 106, second fixed sequence probe 108 and bridging probe 110 is eluted or otherwise separated from nucleic acid 102, and universal oligonucleotide primers 122 are added. Ligation junction 150 between the first fixed sequence probe 106 and the bridging probe 110, and ligation junction 152 between the bridging probe 110 and the second fixed sequence probe 108 are indicated in first ligation product 114. At step 107, universal PCR (uPCR) of the first ligation products is performed, resulting in uPCR product(s) 116. Note ligation junctions 150 and 152 are noted in uPCR product 116 (only one uPCR product 116 is shown). As noted previously, universal priming sequences 112 on the first and second fixed sequence probes (106 and 108, respectively) may be the same, as shown, or may be different, in which case the universal oligonucleotide primers 122 used to perform uPCR would be different. Also, in some embodiments, rather than using both universal priming sequences to amplify the first ligation product 114, a linear amplification is performed utilizing only one of the universal priming sites, or only one fixed sequence oligonucleotide contains a universal priming sequence.

At step 109, a subsequent set of oligonucleotide probes is added to uPCR product 116. The subsequent set of oligonucleotide probes in this embodiment consists of a first fixed sequence probe 126, a second fixed sequence probe 128 and a bridging oligonucleotide probe 130. First 126 and second 128 fixed sequence probes each comprise a universal priming sequence 132, where the universal priming sequence 132 comprises a sequence to allow for universal amplification in a later step, and, like the universal priming sequences in the initial set of oligonucleotide probes, may comprise other sequences useful for manipulating, identifying and/or quantifying the amplification product, and again, the universal priming sequences 132 may be the same sequence or may be different sequences, and if different, in preferred embodiments the melting temperature ($T_m$) of the primers used in any subsequent amplification hybridized to the universal priming sequences are preferably similar. Note that universal priming sequences 112 and 132 may be the same; however, in preferred embodiments they are different so that the only ligation products that are amplified in the second amplification are amplification products that result from ligation of the subsequent set of oligonucleotide probes. Also note that as with the beginning nucleic acid 102, uPCR product 116 optionally may be immobilized to a solid support 118 for ease of isolation or separation from other nucleic acids in subsequent steps.

At step 111, the subsequent set of oligonucleotide probes is allowed to anneal to the region of interest in uPCR product 116, where the first fixed sequence oligonucleotide 126 in the subsequent set anneals 5' in the region of interest, the second fixed sequence oligonucleotide 128 in the subsequent set anneals 3' in the region of interest, and the bridging oligonucleotide 130 in the subsequent set anneals between the first and second fixed sequence oligonucleotides in the region of interest. The arrows on the ends of the first fixed sequence oligonucleotide probe and the bridging oligonucleotide probe indicate that these oligonucleotide probes may be extended by a polymerase and dNTPs if the first and second fixed oligonucleotides and the bridging oligonucleotide of the subsequent set do not anneal completely contiguous to one another in the region of interest. As with the first hybridization reaction, specific embodiments, however, the bringing oligo will anneal immediately adjacent to both the 5' and 3' fixed oligonucleotides.

At step 113, ligation product 136 comprising first fixed sequence probe 126, second fixed sequence probe 128 and bridging probe 130 from the subsequent set is eluted or otherwise separated from uPCR product 116 (e.g., by utilizing solid support or immobilization moiety 118), and universal oligonucleotide primers 134 are added so that ligation product 136 may be amplified using universal priming sequences 132. As before, if the universal priming sequences 132 are different, the universal oligonucleotide primers 134 will be different. Note, as before, that in some embodiments rather than using both universal priming sites (or including universal priming sites in both the first and second fixed sequence oligonucleotides), a linear amplification is performed utilizing only one of the universal priming sites.

The ligation junction 154 between the first fixed sequence probe 126 and the bridging probe 130 of the subsequent set, and the ligation junction 156 between the bridging probe 130 and the second fixed sequence probe 128 of the subsequent set are indicated in ligation product 136, as are the ligation junctions 150, 152 from the first ligation process with the initial set of oligonucleotide probes. Note that the ligation junctions 154 and 156 resulting from the ligation of the subsequent set of oligonucleotide probes are offset from the ligation junctions 150, 152 from the ligation of the initial set of oligonucleotide probes in the region of interest. In this embodiment, the first and second fixed oligonucleotide probes from the subsequent set encompass the ligation junctions 150 and 152. At step 115, universal PCR (uPCR) is performed on ligation product 136 utilizing universal oligonucleotide primers 134, resulting in uPCR products 140, which can then be sequenced.

Figure 1B:
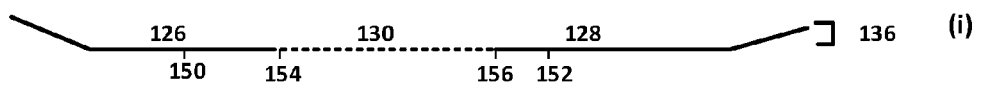
FIG. 1B, schemes (i) through (iv) and (vi) show alternative embodiments for positioning of the subsequent set of oligonucleotide probes vis-à-vis the initial set of oligonucleotide probes, and scheme (v) shows an alternative configuration for initial and/or subsequent probe sets where the fixed sequence oligonucleotide probes of the set are not separate probes.
Figure 1B:
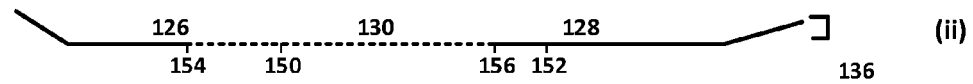
Figure 1B:
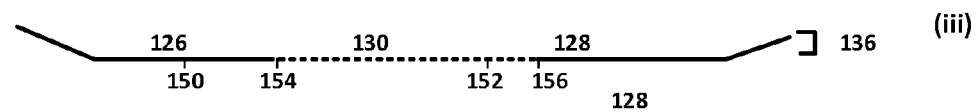
Figure 1B:
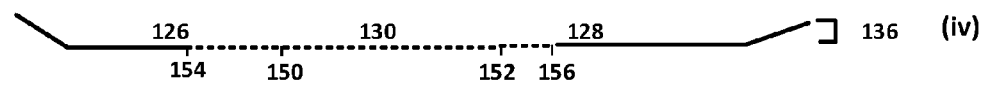
Figure 1B:
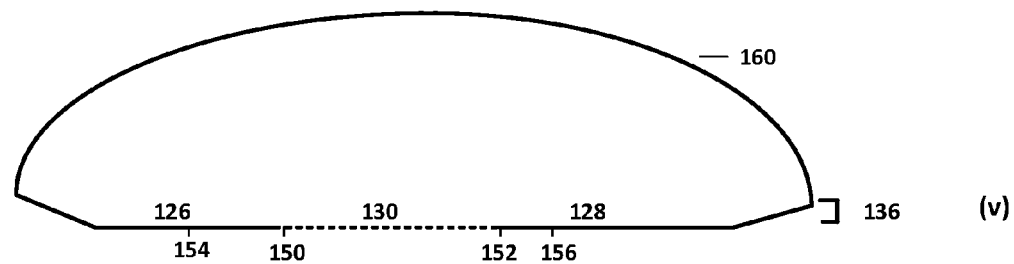
Figure 1B:
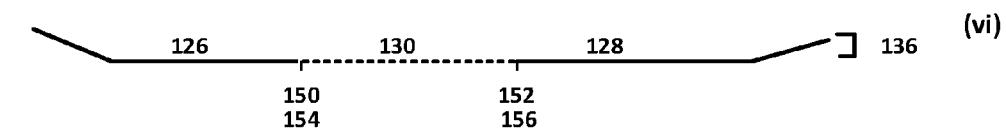

FIG. 1B shows alternative embodiments for positioning of the subsequent set of oligonucleotide probes vis-à-vis the initial set of oligonucleotide probes. In scheme (i) of FIG. 1B, the positioning of the subsequent set of oligonucleotide probes in relation to the initial set of oligonucleotide probes is the same as in FIG. 1A (see the representation between steps 113 and 115 of FIG. 1A). Here, indicated in ligation product 136 are the ligation junction 154 between the first fixed sequence probe 126 and the bridging probe 130 of the subsequent set, and the ligation junction 156 between the bridging probe 130 and the second fixed sequence probe 128 of the subsequent set. Also indicated are ligation junctions 150 and 152 from the first ligation with the initial set of oligonucleotide probes. Note that ligation junctions 154 and 156 resulting from the ligation of the subsequent set of oligonucleotide probes are shifted or offset from the ligation junctions from the ligation of the initial set of oligonucleotide probes in the region of interest. In this scheme (i), the first and second fixed oligonucleotide probes from the subsequent set encompass the ligation junctions 150 and 152; that is, ligation junctions 154 and 156 are located between (flanked by) ligation junctions 150 and 152.

In scheme (ii) of FIG. 1B, the positioning of the subsequent set of oligonucleotide probes in relation to the initial set of oligonucleotide probes is different from that seen in FIG. 1A. Again, indicated in ligation product 136 are the ligation junction 154 between the first fixed sequence probe 126 and the bridging probe 130 of the subsequent set, and the ligation junction 156 between the bridging probe 130 and the second fixed sequence probe 128 of the subsequent set. Also indicated are the ligation junction 150 resulting from ligation between the first fixed sequence probe 106 and the bridging probe 110 of the initial set and ligation junction 152 resulting from ligation between the bridging probe 110 and the second fixed sequence probe 108 from the initial set of oligonucleotide probes. Again in this embodiment, the ligation junctions 154 and 156 resulting from the ligation of the subsequent set of oligonucleotide probes are shifted or offset from the ligation junctions from the ligation of the initial set of oligonucleotide probes in the region of interest. However, in this scheme (ii), the first and second fixed oligonucleotide probes from the subsequent set do not encompass both ligation junctions 150 and 152. Instead, ligation junction 154 is outside of (5') ligation junction 150, though ligation junction 156 is inside (5') that of ligation junction 152.

Scheme (iii) of FIG. 1B is similar to scheme (i) and (ii) in the sense that the ligation junctions 154 and 156 resulting from the ligation of the subsequent set of oligonucleotide probes are shifted or offset from the ligation junctions from the ligation of the initial set of oligonucleotide probes in the region of interest. However, unlike scheme (i) but similar to scheme (ii), the first and second fixed oligonucleotide probes from the subsequent set do not encompass both ligation junctions 150 and 152. Instead, ligation junction 156 is outside of (3') ligation junction 152, though ligation junction 154 is inside (3') that of ligation junction 150.

Scheme (iv) of FIG. 1B again is similar to schemes (i), (ii) and (iii) in the sense that the ligation junctions 154 and 156 resulting from the ligation of the subsequent set of oligonucleotide probes are shifted or offset from the ligation junctions from the ligation of the initial set of oligonucleotide probes in the region of interest; however, here neither the first nor second fixed oligonucleotide probes from the subsequent set encompass ligation junctions 150 and 152. Instead, ligation junctions 154 and 156 fall outside (that is, 5' and 3', respectively) of ligation junctions 150 and 152.

Scheme (v) of FIG. 1B shows an alternative exemplary embodiment that may be used for the initial and/or offset oligonucleotide probe sets where the fixed sequence oligonucleotide probes of the set are not separate probes, but are instead precircle type probes. Again note that the ligation junctions 154 and 156 resulting from the ligation of the subsequent set of oligonucleotide probes are shifted or offset from the ligation junctions from the ligation of the initial set of oligonucleotide probes in the region of interest. And, like scheme (iv), neither the first nor second fixed oligonucleotide probes from the subsequent set encompass ligation junctions 150 and 152. Instead, ligation junctions 154 and 156 fall outside (that is, 5' and 3', respectively) of ligation junctions 150 and 152. The nucleic acid portion of the fixed sequence probe that connects the first and second fixed probes 126 and 128 is designed 160.

Scheme (vi) of FIG. 1B is dissimilar to schemes (i) through (v) in the sense that the ligation junctions 154 and 156 resulting from the ligation of the subsequent set of oligonucleotide probes are not both shifted or offset from the ligation junctions from the ligation of the initial set of oligonucleotide probes in the region of interest; that is, here the first fixed oligonucleotide probes from the initial and subsequent sets encompass one or both of the same ligation junctions 150 and 154, the second fixed oligonucleotide probes from the initial and subsequent sets encompass one or both of the same ligation junctions 152 and 156.

In some embodiments, the bridging oligonucleotide probes of the initial set and subsequent sets of oligonucleotide probes are different lengths, as would have to be the case in schemes (i) and (iv) of FIG. 1B; however, in some embodiments, the bridging probes of the initial and subsequent sets of oligonucleotide probes are the same, as would be the case in scheme (vi) of FIG. 1B, and could be the case in scheme (ii), where the bridging oligonucleotide probe of the subsequent set is positioned 5' of the bridging oligonucleotide primer of the initial set, or scheme (iii), where the bridging oligonucleotide probe of the subsequent set is positioned 3' of the bridging oligonucleotide primer of the initial set.

Figure 2:
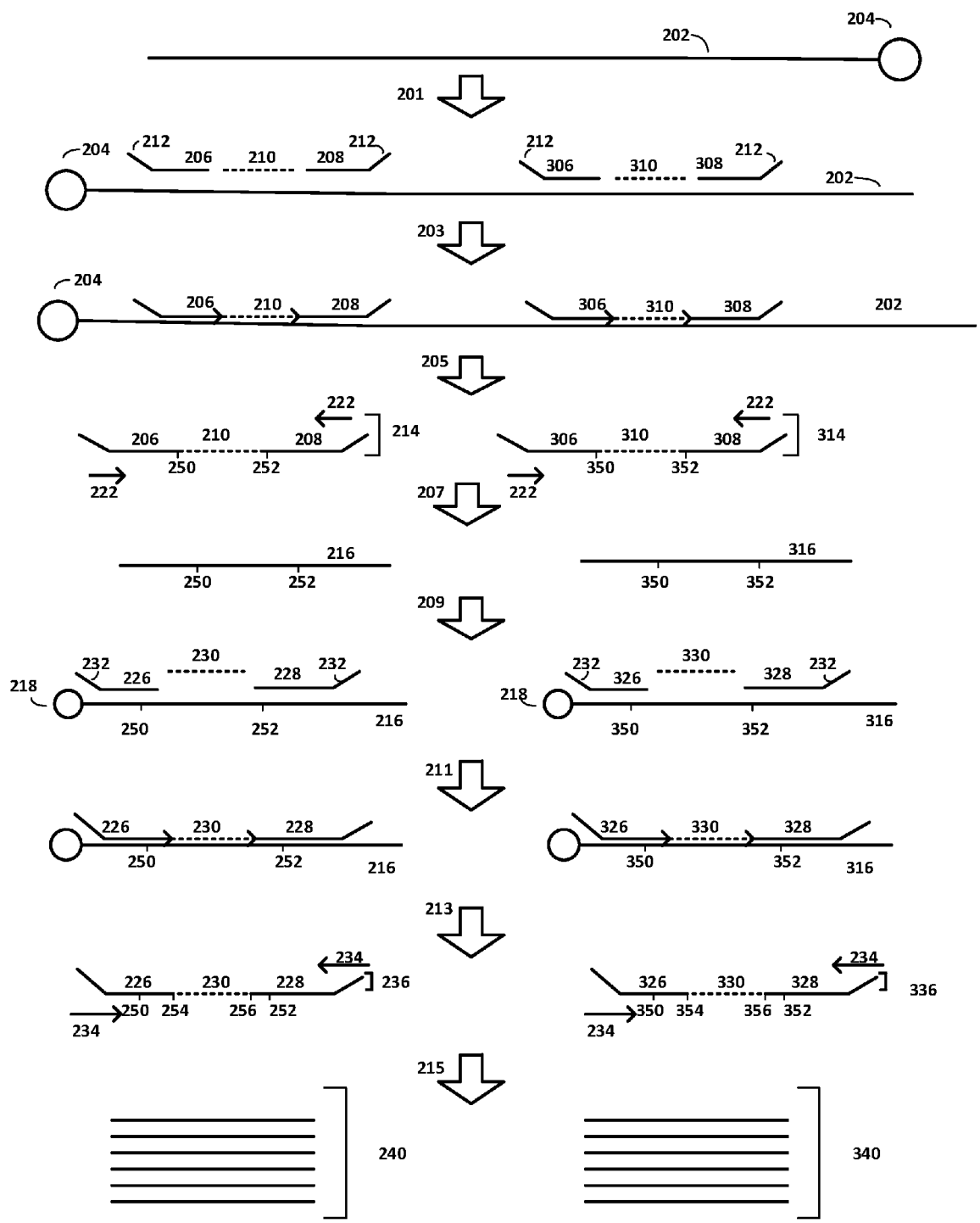
FIG. 2 is a simplified schematic of one embodiment of the multiplexed sequential ligation-based analysis methods of the present invention where two different regions of interest are being interrogated.

FIG. 2 is a simplified schematic of one embodiment of the multiplexed sequential ligation-based analysis methods of the present invention where two different regions of interest are being interrogated. This embodiment of the invention is exemplary for two regions of interest, but in practice the methods of the invention may be multiplexed to interrogate 10 regions of interest or more, 12 regions of interest or more, or 24, 48, 60, 96, 128, 200, 400, 500, 1000, 2500, or 5000 regions of interest or more. The regions of interest all may be located on the same chromosome, or, in most embodiments, the regions of interest are located on one or more different chromosomes.

FIG. 2 shows a method 200, where a nucleic acid 202 comprising two regions of interest are optionally immobilized to solid support 204. Such immobilization of nucleic acid 202 and of other nucleic acids in subsequent steps is in fact not used in preferred embodiments. At step 201, a first and second initial set of oligonucleotide probes is added to the nucleic acid 202. The first initial set of oligonucleotide probes consists of a first fixed sequence probe 206, a second fixed sequence probe 208 and a bridging oligonucleotide probe 210. The second initial set of oligonucleotide probes consists of a first fixed sequence probe 306, a second fixed sequence probe 308 and a bridging oligonucleotide probe 310. The first 206 and 306 and second 208 and 308 fixed sequence probes from each initial set comprise a universal priming sequence 212. Universal priming sequence 212 comprises a sequence to allow for universal amplification in a later step of ligation products from both initial sets of oligonucleotide probes. As in FIG. 1A, universal priming sequences 212 may be the same or may be different. In a multiplexed reaction, typically the universal priming sequence for the 5' fixed oligonucleotide probe of each of the initial sets of oligonucleotide probes will be the same, and the universal priming sequences for the 3' fixed oligonucleotide probes of each of the initial sets of oligonucleotide probes will be the same. However, in some embodiments, the universal priming sequences in different sets of initial oligonucleotide probes will be different (that is, not all 5' universal priming sequences will be the same and not all 3' sequences will be the same). As described previously, in preferred embodiments the melting temperatures of the universal priming sequences will be similar.

At step 203, both initial sets of oligonucleotide probes are allowed to anneal to their respective regions of interest in the nucleic acid 202, where the first fixed sequence oligonucleotide 206 and 306 in each of the initial sets anneals 5' in the respective region of interest, the second fixed sequence oligonucleotide 208 and 308 in each of the initial sets anneals 3' in the respective region of interest, and the bridging oligonucleotide 210 and 310 in each of the initial sets anneals between the first and second fixed sequence oligonucleotides in the respective region of interest. The arrows on the ends of the first fixed sequence oligonucleotide probes 206 and 306 and the bridging oligonucleotide probes 210 and 310 indicate that these oligonucleotide probes may be extended by a polymerase and dNTPs if the first and second fixed oligonucleotides and the bridging oligonucleotide of the initial sets do not anneal completely contiguous to one another in the regions of interest.

At step 205, ligation product 214 comprising first fixed sequence probe 206, second fixed sequence probe 208 and bridging probe 210, and ligation product 314 comprising first fixed sequence probe 306, second fixed sequence probe 308 and bridging probe 310, are eluted or otherwise separated from nucleic acid 202 (in this embodiment, such separation may be effected by solid support 204), and universal oligonucleotide primers 222 are added. The ligation junction 250 between the first fixed sequence probe 206 and the bridging probe 210, and the ligation junction 252 between the bridging probe 210 and the second fixed sequence probe 208 of the first set of initial oligonucleotide probes are indicated in ligation product 214, and the ligation junction 350 between the first fixed sequence probe 306 and the bridging probe 310, and the ligation junction 352 between the bridging probe 310 and the second fixed sequence probe 308 of the second set of initial oligonucleotide probes are indicated in ligation product 314. At step 207, universal PCR (uPCR) is performed on ligation products 214 and 314 using universal oligonucleotide primers 222, resulting in uPCR products 216 and 316. Note ligation junctions 250 and 252 are noted in uPCR product 216 and ligation junctions 350 and 352 are noted in uPCR product 316. Note that in some embodiments rather than using both universal priming sites (or including universal priming sites in both the first and second fixed sequence oligonucleotides), a linear amplification is performed utilizing only one of the universal priming sites.

At step 209, two subsequent sets of oligonucleotide probes are added to uPCR products 216 and 316. The first subsequent set of oligonucleotide probes consists of a first fixed sequence probe 226, a second fixed sequence probe 228 and a bridging oligonucleotide probe 230, and the second subsequent set of oligonucleotide probes consists of a first fixed sequence probe 326, a second fixed sequence probe 328 and a bridging oligonucleotide probe 330. First fixed sequence probes 226 and 326 and second fixed sequence probes 228 and 328 each comprise a universal priming sequence 232, where the universal priming sequence 232 comprises, in addition to other sequences in some embodiments, a sequence to allow for universal amplification in a later step. As described, universal priming sequence 232 may be the same for each fixed sequence oligonucleotide probe or may be different, or may be the same for each of the 5' fixed sequences probes and the same for each of the 3' fixed sequence probes but different for 5' and 3' fixed sequence probes. Note that as with beginning nucleic acid 202, uPCR products 216 and 316 may be immobilized to a solid support 318 for ease of isolation or separation from other nucleic acids in subsequent steps.

At step 211, first and second subsequent sets of oligonucleotide probes are allowed to anneal to their respective regions of interest in uPCR products 216 and 316, where the first fixed sequence oligonucleotide 226 and 326 in each of the subsequent sets anneals 5' to the respective uPCR product 216 and 316, the second fixed sequence oligonucleotide 228 and 328 in each of the subsequent sets anneals 3' in the respective uPCR product 216 and 316, and the bridging oligonucleotide 230 and 330 in each of the subsequent sets anneals between the first and second fixed sequence oligonucleotides in the respective uPCR product 216 and 316. The arrows on the ends of the first fixed sequence oligonucleotide probes 226 and 326 and the bridging oligonucleotide probes 220 and 320 indicate that these oligonucleotide probes may be extended by a polymerase and dNTPs if the first and second fixed oligonucleotides and the bridging oligonucleotide of the subsequent sets do not anneal completely contiguous to one another in the regions of interest.

At step 213, ligation product 236 comprising the first fixed sequence probe 226, the second fixed sequence probe 228 and the bridging probe 230 from the first set of subsequent oligonucleotide probes is eluted or otherwise separated from uPCR product 216 (e.g., by utilizing solid support or immobilization moiety 218). Also, ligation product 336 comprising the first fixed sequence probe 326, the second fixed sequence probe 328 and the bridging probe 330 from the second set of subsequent oligonucleotide probes is eluted or otherwise separated from uPCR product 316 (e.g., by utilizing solid support or immobilization moiety 218).

Universal oligonucleotide primers 234 are then added so that ligation products 236 and 336 may be amplified using universal priming sequences 232. Note that universal priming sequences 212 and 232 may be the same; however, in preferred embodiments they are different so that the only ligation products that are amplified in the second amplification are amplification products that result from ligation of the subsequent set of oligonucleotide probes. The ligation junction 254 between the first fixed sequence probe 226 and the bridging probe 230 of the first subsequent set, and the ligation junction 256 between the bridging probe 230 and the second fixed sequence probe 228 of the first subsequent set are indicated in ligation product 236, as are the ligation junctions 250 and 252 from the first ligation process with the first initial set of oligonucleotide probes. In addition, the ligation junction 354 between the first fixed sequence probe 326 and the bridging probe 330 of the second subsequent set, and the ligation junction 356 between the bridging probe 330 and the second fixed sequence probe 328 of the second subsequent set are indicated in ligation product 336, as are the ligation junctions 350 and 352 from the first ligation process with the second initial set of oligonucleotide probes. Note that the ligation junctions 254, 256 and 354, 356 resulting from the ligation of the first and second subsequent sets of oligonucleotide probes are offset from the ligation junctions 250, 252 and 350, 352 from the ligation of the first and second initial sets of oligonucleotide probes in the regions of interest. In this embodiment, like FIG. 1A and scheme (i) of FIG. 1B, the first and second fixed oligonucleotide probes from each of the subsequent sets encompass the ligation junctions 250, 350 and 252, 352. At step 215, uPCR is performed on ligation products 236 and 336 using universal oligonucleotide primers 234, resulting in uPCR products 240 and 340, which are then sequenced in whole or in part and described infra.

It should be noted that though FIG. 1A, FIG. 1B and FIG. 2 exemplify methods of the invention utilizing one bridging oligonucleotide probe, more than one bridging oligonucleotide probe may be utilized. Also, although FIG. 2 exemplifies the analysis of two regions of interest, in practice the methods of the invention may be multiplexed to interrogate 10 regions of interest or more, 12 regions of interest or more, or 24, 28, 60, 96, 128, 200, 400, 500, 1000, 2500, or 5000 regions of interest or more from a sample. Further, though FIGS. 1A and 2 exemplify a method comprising the hybridization, ligation and amplification of an initial set of oligonucleotide probes and one subsequent set of oligonucleotide probes for each region of interest, additional rounds of hybridization, ligation and amplification may be performed on one or more of the regions of interest with additional sets of subsequent oligonucleotide probes. Moreover, though both FIG. 1A and FIG. 2 include an amplification (uPCR) step at steps 107 and 207 (amplifying the ligation product of the first and second oligonucleotide and bridging oligonucleotide probes of the initial set of oligonucleotide probes), this amplification step is optional, though it is preferred. Similarly, though amplification of the ligation product of the first and second oligonucleotide and bridging oligonucleotide probes in the subsequent set of probes prior to sequencing is preferred, it also is optional.

In addition, the methods of the invention may be carried out where either both of the initial and subsequent sets of oligonucleotide probes do not comprise a bridging oligonucleotide probe; that is, either or both of the initial and subsequent sets of oligonucleotide probes comprise first and second fixed sequences probes only, which may or may not hybridize in a contiguous manner. If the first and second fixed sequence oligonucleotides from either the initial or subsequent sets do not hybridize contiguously, an extension step is performed before the ligation step is performed. Moreover, the methods may comprise a combination of these embodiments; that is, the initial set of oligonucleotide probes may consist of two fixed oligonucleotide probes and a bridging probe, where the subsequent set of oligonucleotide probes consists of two fixed oligonucleotide probes, where one or more of the oligonucleotide probes in either set requires extension. Further, the sets of oligonucleotide probes may vary in character from region to region of interest (that is, in addition to the sequence differences).

FIGS. 1A, 1B and 2 thus provide simplified illustrations of the steps for multiplexed sequential ligation-based analyses of subsequent ligation products of the invention. Specifics of the components are described infra.

Regions of Interest

The length of the regions of interest in the target nucleic acid in most embodiments are of a sufficient length to provide enough sequence information to distinguish the regions of interest from one another and from other sequences that may be present in the target nucleic acid. Generally, a region of interest is at least about 16 nucleotides in length, and more typically, a region of interest is at least about 20 nucleotides in length. In a preferred aspect of the invention, the regions of interest are at least about 30, 32, 40, 45, 50, or 60 nucleotides in length. In other aspects of the invention, the regions of interest can be about 100, 150, 200 or up to 250 or more nucleotides in length.

With genomic DNA samples, most often the DNA must be fragmented. In the practice of the methods of the present invention, fragmentation of the DNA sample can be accomplished by any means known to those of ordinary skill in the art. Preferably, the fragmenting is performed by enzymatic or mechanical means. Mechanical means may be sonication or physical shearing, and enzymatic means may be digestion with nucleases (e.g., Deoxyribonuclease I (DNase I)) or one or more restriction endonucleases.

In many aspects of the invention, the target nucleic acid comprising the regions of interest (or, e.g., one or more oligonucleotide probes in a set of oligonucleotide probes or one or more ligation or amplification products) are immobilized to facilitate separation of reactants and reaction products. Such immobilization is optional but is employed in preferred embodiments. Immobilization of the genomic or cell-free DNA (the target nucleic acid) or one or more oligonucleotide probes in a set of oligonucleotide probes or one or more ligation or amplification products can be accomplished by covalently or noncovalently attaching the nucleic acids to a solid phase support (e.g., a bead) using methods well known in the art; for example, by using streptavidin or avidin/biotin linkages, carbamate linkages, ester linkages, or amide, thiolester, (N)-functionalized thiourea, functionalized maleimide, amino, disulfide, amide, or hydrazone linkages, among others. The target nucleic acid—or one or more oligonucleotide probes in a set of oligonucleotide probes or one or more ligation or amplification products—may be directly linked to the support, or preferably are indirectly linked, e.g., through a linker moiety directly linked to the support. Antibodies that specifically bind to nucleic acids can also be employed as linking moieties. In addition, a silyl moiety can be used to attach a nucleic acid directly to a solid substrate using methods known in the art. Again, immobilization of one or more of the target nucleic acids or one or more oligonucleotide probes in a set of oligonucleotide probes or one or more of the ligation or amplification products may be used to facilitate separation of the reactants and products at various steps in the methods.

Oligonucleotide Probes and Probe Sets

The initial and subsequent sets of probes each comprise, in some embodiments, a first fixed sequence oligonucleotide probe, a second fixed sequence oligonucleotide probe, and one or more bridging oligonucleotide probes. For example, in some embodiments, the initial sets of oligonucleotide probes consist of a first fixed sequence oligonucleotide probe, a second fixed sequence oligonucleotide probe, and more than one bridging oligonucleotide probes where the bridging oligonucleotide probe is engineered to detect polymorphisms. In embodiments where both nonpolymorphic and polymorphic regions of interest are detected, the initial sets of oligonucleotide probes for the regions of interest often will vary, where for nonpolymorphic sites, the initial set of oligonucleotide probes will consist of a first fixed sequence oligonucleotide probe, a second fixed sequence oligonucleotide probe, and a single bridging oligonucleotide probe, and wherein for polymorphic sites, the initial set of oligonucleotide probes will consist of a first fixed sequence oligonucleotide probe, a second fixed sequence oligonucleotide probe, and more than one bridging oligonucleotide probe. Alternatively, for polymorphic sites, one fixed sequence oligonucleotide and the bridging oligonucleotides may be the same for each set, but one of the fixed sequence oligonucleotides contains the polymorphic nucleotide, most often at or near the end of the fixed sequence oligonucleotide that becomes ligated to the bridging oligonucleotide. Similarly, the subsequent sets of oligonucleotide probes may consist of a first fixed sequence oligonucleotide probe, a second fixed sequence oligonucleotide probe, and one bridging oligonucleotide probe, which is preferred, or the subsequent sets of oligonucleotide probes may consist of a first fixed sequence oligonucleotide probe, a second fixed sequence oligonucleotide probe, and more than one bridging oligonucleotide probe. Or, as described, the initial or subsequent sets of oligonucleotides may consist of first and second fixed oligonucleotides only.

As described, polymorphisms or SNPs may be detected using initial sets of oligonucleotide probes with differing bases appropriate for differential detection of SNPs, or polymorphisms and SNPs may be detected using initial sets of oligonucleotide probes that are the same, and the sequencing step at the end of the methods provides that sequence information identifying the SNPs in a region of interest.

At least one of the fixed sequence oligonucleotide probes of the initial sets or the subsequent sets of oligonucleotide probes comprise a portion that is complementary to the regions of interest being interrogated, and a portion that comprises the universal priming sequence used for amplification of the ligation products and in some embodiments, both fixed sequence oligonucleotide probes will comprise universal priming sequences. The portion of the fixed sequence oligonucleotide probes that comprises the universal priming sequence may also comprise one or more indices as described below and/or other sequences that allow for the manipulation, identification and/or quantification of the ligation or amplification products resulting from the methods. The portion of the fixed sequence oligonucleotide probes that is complementary to the regions of interest being interrogated is typically 10 to 50 nucleotides in length, more typically 15 to 35 nucleotides in length, or 18 to 28, 20 to 26, or 22 to 24 nucleotides in length. The length of the portion of the fixed sequence oligonucleotide probes that comprises the universal priming sequence depends on what sequences are encompassed by this portion; that is, the length depends on what additional sequence elements are encompassed within this portion in addition to the universal priming sequence. Typically, the length of the portion of the fixed sequence oligonucleotide probes that comprises the universal priming sequence is 10 to 50 nucleotides in length, more typically 15 to 35 nucleotides in length, or 18 to 28, 20 to 26, or 22 to 24 nucleotides in length.

In certain aspects the universal priming regions of the fixed sequence oligonucleotides are associated with one or more indexes or indices that, e.g., identify the regions of interest and/or a particular sample being analyzed. The detection of the one or more of these indices can serve as a surrogate for detection of the entire region of interest, or detection of an index may serve as confirmation of the presence of a particular region of interest if both the sequence of the index and the sequence of the nucleic acid region itself are determined.

Indices are typically non-complementary, unique sequences contained within the universal priming region of the first and/or second fixed oligonucleotide probes in a set to provide information relevant to the region of interest that anneals to the probe. In preferred aspects of the invention using indices, universal priming regions are designed so that the one or more indices are coded in the universal priming regions or as a part of the universal primer. The order and placement of indices, as well as the length of indices, can vary, and they can be used in various combinations. The advantage of employing indices is that the presence (and ultimately the quantity or frequency) of a region of interest can be obtained without the need to sequence an entire amplified ligation product corresponding to the region of interest, although in certain aspects it may be desirable to do so. Generally, however, the ability to identify and quantify a region of interest through identification of one or more indices will decrease the length of sequencing required, particularly if the index sequence is captured at the 3' or 5' end of the amplified ligation product proximal to where a sequencing probe is located. Use of indices as a surrogate for identification of regions of interest also may reduce sequencing errors since longer sequencing reads are more prone to the introduction of error.

One example of an index is a locus index. A locus index typically is unique for each region of interest so that quantification of the number of times a particular locus index occurs in a sample can be related to the relative number of copies of the corresponding region of interest selected. Generally, the locus index is long enough to label each known region of interest uniquely. For instance, if the method interrogates 192 known regions of interest, there are at least 192 unique locus indexes, each uniquely identifying a region of interest. The locus index may contain additional nucleotides that allow for identification and correction of sequencing errors including the detection of deletion, substitution, or insertion of one or more bases during sequencing as well as nucleotide changes that may occur outside of sequencing such as oligonucleotide synthesis, amplification, or any other aspect of the methods.

Another example of an index is an allele index, typically as an alternative to or occasionally in addition to a locus index. An allele index is unique for a particular allele of a region of interest, so that quantification of the number of times a particular allele index occurs in a sample can be related to the relative number of copies of that allele in the target nucleic acid, and the summation of the allelic indices can be related to the relative number of copies of that region of interest.

In yet another example, an identification index may be provided. In such an aspect, a sufficient number of identification indices are present to uniquely identify each amplified ligation product made from the initial set of oligonucleotide probes in the sample. Identification index sequences are preferably 6 or more nucleotides in length. In a preferred aspect, the identification index is long enough to have statistical probability of labeling each ligation product from an initial set of oligonucleotide probes with a unique identification index. For example, if there are n total copies of all regions of interest, there are substantially more than n identification indexes such that each molecule interrogated is likely to be labeled with a unique identification index.

The identification index—like the other indices—may be combined with any other index to create one index that provides information for two properties. The identification locus may also be used to detect and quantify amplification bias that may occur downstream of the initial isolation of the regions of interest from a sample and this data may be used to normalize the sample data.

In addition to the other indices described herein, a correction index may be employed. A correction index is a short nucleotide sequence that allows for correction of amplification, sequencing or other experimental errors including the detection of a deletion, substitution, or insertion of one or more bases during sequencing as well as nucleotide changes that may occur outside of sequencing such as oligonucleotide synthesis, amplification, or in other aspects of the assay. Correction indices may be stand-alone indices that are separate sequences, or they may be embedded within other indices to assist in confirming accuracy of the experimental techniques used, e.g., a correction index may be a subset of sequences of a locus index or an identification index.

In some aspects, indices that indicate the target nucleic acid or sample from which the regions of interest are isolated are used to identify the source of the regions of interest in a multiplexed assay system. In such aspects, the regions of interest from one individual will be assigned to and associated with a particular unique sample index. The sample index can thus be used to assist in nucleic acid region identification when multiplexing different samples in a single reaction vessel, such that each sample can be identified based on its sample index. In a preferred aspect, there is a unique sample index for each target nucleic acid in a set of samples, and the samples are pooled during sequencing. For example, if twelve samples are pooled into a single sequencing reaction, there are at least twelve unique sample indexes such that each sample is labeled uniquely. After the sequencing step is performed, the sequencing data preferably is first segregated by sample index prior to determining the frequency of each the region of interest for each sample and prior to determining whether there is a chromosomal abnormality for each sample.

The bridging oligonucleotide probes for an initial set or subsequent set of oligonucleotide probes can be varied in configuration. For example, in the methods shown in FIGS. 1 and 2, the bridging oligonucleotide probes are sequence-specific for a region of interest and of similar length. However, in some embodiments, the bridging oligonucleotides of a set may be composed of a mixture of oligonucleotide probes with degeneracy in each of the positions, so that this mixture of randomer bridging oligonucleotide probes is compatible with all sets of fixed sequence oligonucleotide probes in a multiplexed assay. For example, in the case where 5-base bridging oligonucleotide probes are used, the number of unique bridging oligonucleotide probes would be $4^5=1024$. Thus, the number of bridging oligonucleotide probes would be independent of the number of regions of interest since all possible bridging oligonucleotide probes would be present in the reaction. In another embodiment, the bridging oligonucleotide probes can vary in length so that certain of the bridging oligonucleotide probes in a mixture of bridging oligonucleotide probes will be compatible with particular sets of fixed sequence oligonucleotides.

In the detection of polymorphisms, fixed sequence oligonucleotides or bridging oligonucleotides of differing sequence may be utilized, as taught in U.S. Ser. No. 13/013,732, filed Jan. 25, 2011; Ser. No. 13/245,133, filed Sep. 26, 2011; Ser. No. 13/205,570, filed Aug. 8, 2011; Ser. No. 13/293,419, filed Nov. 10, 2011; Ser. No. 13/205,409, filed Aug. 8, 2011; Ser. No. 13/205,603, filed Aug. 8, 2011; Ser. No. 13/407,978, filed Feb. 29, 2012; Ser. No. 13/274,309, filed Oct. 15, 2011; Ser. No. 13/316,154, filed Dec. 9, 2011, and Ser. No. 13/338,963, filed Dec. 28, 2011, all of which are incorporated herein in their entirety. For example, the bridging oligonucleotide probes can possess different sequences corresponding to single nucleotide polymorphisms, and ligation reactions are optimized for those oligonucleotide probe sets that comprise the specific sequence provided by a bridging oligonucleotide probe. Also, the invention contemplates use of initial and subsequent sets of oligonucleotide probes with first and second fixed sequence oligonucleotide probes but without one or more bridging oligonucleotide probes, Though the embodiments illustrated in FIGS. 1A and 2 show the fixed sequence oligonucleotide probes and the bridging oligonucleotide probes of a set being allowed to anneal simultaneously, the bridging oligonucleotide probes may instead be added to the annealing reaction after the fixed sequence oligonucleotide probes have annealed, optionally following the removal of unhybridized fixed sequence oligonucleotide probes. The conditions of the hybridization or annealing reactions are preferably optimized near the $T_m$ of the bridging oligonucleotide probes to prevent erroneous hybridization of bridging oligonucleotide probes that are not fully complementary to the region of interest. The bridging oligonucleotide probes may be of various lengths depending on the target nucleic acids. Typically the bridging oligo is from 3 to 32 nucleotides in length, but in specific examples, they can be from 10 to 30 nucleotides in length, more typically 15 to 25 nucleotides in length, 5-10 nucleotides in length, 4 to 9 nucleotides in length, 18 to 28 nucleotides in length, 20 to 26 nucleotides in length, or 22 to 24 nucleotides in length.

Amplification and Sequencing Techniques

Amplification or enrichment techniques that may be employed in the multiplexed sequential ligation-based analysis methods of the invention include numerous techniques that enhance the overall concentration of the ligation products at various steps in the analysis methods and prior to sequence determination. Such techniques include straightforward techniques such as PCR, as well as techniques that themselves provide additional selection options or other benefits. Examples of such techniques are described below.

In preferred aspects of the invention, universal amplification is used to amplify (either linearly or exponentially) the ligation products created following hybridization of the fixed sequence oligonucleotides and the bridging oligonucleotides in both the initial sets of oligonucleotide probes and in the subsequent sets of oligonucleotide probes. Universal priming sequences are included in the ligation products so that they may be amplified in a single universal amplification reaction, typically by way of including a universal priming sequence in the fixed sequence oligonucleotide probes, although universal priming sequences may also be ligated to the proximal ends of the ligation products. The inclusion of universal priming sequences in the fixed sequence oligonucleotide probes allows a subsequent controlled universal amplification of all or a portion of the ligation products prior to a subsequent round of hybridization, ligation and amplification with an subsequent set of oligonucleotide probes or prior to sequencing.

Preferably, the first ligation products of the initial sets of oligonucleotide probes are enriched by a linear reaction. The first enrichment step consists of 2-30 cycles, with each cycle commonly consisting of 2-3 discrete temperature steps, usually three. The cycling is often preceded by a single initiation step at a high temperature (>90° C.), and followed by one hold step at the end for final product extension. The temperatures used and the length of time applied in each cycle depend on a variety of parameters known in the art, including the enzyme used for DNA synthesis, the concentration of divalent ions and dNTPs in the reaction, and the melting temperature ($T_m$) of the primers. The second ligation products of the subsequent sets of oligonucleotide probes can be enriched by either a linear reaction or an exponential reaction, or a linear reaction followed by an exponential reaction.

Bias and variability can be introduced during DNA amplification, such as that seen during polymerase chain reaction (PCR). In cases where an amplification reaction is multiplexed, there is the potential that regions of interest will amplify at different rates or efficiency. Part of this may be due to the variety of primers in a multiplex reaction with some having better efficiency (i.e. hybridization) than others, or some working better in specific experimental conditions due to the base composition. Universal primers for a given locus may behave differently based on sequence of ligation product, buffer conditions, and other conditions.

When performing the amplification steps of the present invention, the whole ligation reaction or an aliquot of the ligation reaction may be used for the universal amplification. Using an aliquot allows different amplification reactions to be undertaken using the same or different conditions (e.g., polymerase, buffers, and the like), e.g., to ensure that bias is not inadvertently introduced due to experimental conditions. In addition, variations in primer concentrations may be used to effectively limit the number of sequence specific amplification cycles. Examples of multiplexing methods used to amplify and/or genotype a variety of samples simultaneously, such as those described in Oliphant et al., U.S. Pat. No. 7,582,420.

Exemplary amplification techniques are described in, e.g., Barany et al., U.S. Pat. Nos. 6,852,487, 6,797,470, 6,576,453, 6,534,293, 6,506,594, 6,312,892, 6,268,148, 6,054,564, 6,027,889, 5,830,711, 5,494,810, describe the use of the ligase chain reaction (LCR) assay for the detection of specific sequences of nucleotides in a variety of nucleic acid samples; Barany et al., U.S. Pat. Nos. 7,807,431, 7,455,965, 7,429,453, 7,364,858, 7,358,048, 7,332,285, 7,320,865, 7,312,039, 7,244,831, 7,198,894, 7,166,434, 7,097,980, 7,083,917, 7,014,994, 6,949,370, 6,852,487, 6,797,470, 6,576,453, 6,534,293, 6,506,594, 6,312,892, and 6,268,148 describe the use of the ligase detection reaction with detection reaction ("LDR") coupled with polymerase chain reaction ("PCR") for nucleic acid detection; Barany et al., U.S. Pat. Nos. 7,556,924 and 6,858,412, describe the use of precircle probes (also or "multi-inversion probes") with coupled ligase detection reaction ("LDR") and polymerase chain reaction ("PCR") for nucleic acid detection; Barany et al., U.S. Pat. Nos. 7,807,431, 7,709,201, and 7,198, 814 describe the use of combined endonuclease cleavage and ligation reactions for the detection of nucleic acid sequences; Willis et al., U.S. Pat. Nos. 7,700,323 and 6,858,412, describe the use of precircle probes in multiplexed nucleic acid amplification, detection and genotyping; and Ronaghi et al., U.S. Pat. No. 7,622,281 describes amplification techniques for labeling and amplifying a nucleic acid using an adapter comprising a unique probe and a barcode.

Once the amplified ligation products from the final round of hybridization, ligation and amplification are made, they are used as templates for sequencing. Numerous methods of sequence determination are compatible with the methods of the invention; preferably, such methods include "next generation" methods of sequencing. Exemplary methods for sequence determination include, but are not limited to, hybridization-based methods, such as disclosed in Drmanac, U.S. Pat. Nos. 6,864,052; 6,309,824; 6,401,267 and U.S. Pub. No. 2005/0191656; sequencing-by-synthesis methods, such as disclosed by, e.g., Nyren et al, U.S. Pat. No. 7,648,824, 7,459,311 and 6,210,891; Balasubramanian, U.S. Pat. Nos. 7,232,656 and 6,833,246; Quake, U.S. Pat. No. 6,911,345; Li et al, PNAS, 100: 414-19 (2003) and as commercialized in TruSeq™ and HiSeq™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.; pyrophosphate sequencing as described in Ronaghi et al., U.S. Pat. Nos. 7,648,824; 7,459,311; 6,828,100 and 6,210,891, and as commercialized by 454 Life Sciences, Inc., Branford, Conn.; ligation-based sequencing determination methods, such as disclosed by, e.g., Drmanac et al., U.S. Pub. No. 2010/0105052, and Church et al, U.S. Pub. Nos. 2007/0207482 and 2009/0018024 for example, and as commercialized in the SOLiD™ technology, Life Technology, Inc., Carlsbad, Calif., and like highly-parallelized sequencing methods, all references of which are incorporated by reference herein in their entirety.

Alternatively, regions of interest can be selected and/or identified using hybridization techniques. Methods for conducting polynucleotide hybridization assays for detection of nucleic acids have been well developed in the art. Hybridization assay procedures and conditions will vary depending on the application and are selected in accordance with the general binding methods known including those referred to in: Maniatis et al., *Molecular Cloning: A Laboratory Manual* (2nd Ed. Cold Spring Harbor, N.Y., 1989); Berger and Kimmel, *Methods in Enzymology*, Vol. 152, Guide to Molecular Cloning Techniques (Academic Press, Inc., San Diego, Calif., 1987); and Young and Davis, PNAS, 80:1194 (1983). Methods and apparatus for carrying out repeated and controlled hybridization reactions have been described in, e.g., U.S. Pat. Nos. 5,871,928; 5,874,219; 6,045,996; 6,386,749 and 6,391,623.

Methods and apparatus for signal detection and processing of intensity data are disclosed in, for example, U.S. Pat. Nos. 5,143,854; 5,547,839; 5,578,832; 5,631,734; 5,800,992; 5,834,758; 5,856,092; 5,902,723; 5,936,324; 5,981,956; 6,025,601; 6,090,555; 6,141,096; 6,185,030; 6,201,639; 6,218,803 and 6,225,625, in U.S. Ser. No. 60/364,731 and in PCT Application PCT/US99/06097 (published as WO99/47964).

Detecting Fetal Copy Number Variation

The multiplexed sequential ligation-based analysis methods of the present invention are particularly suited for identifying copy number variations in a fetus. This includes copy number variations in fetal DNA from a maternal sample, including chromosomal abnormalities including but not limited to aneuploidies such as monosomies and trisomies. Thus, in certain embodiments, the samples tested are maternal samples comprising both maternal and fetal DNA such as maternal blood samples (i.e, whole blood, serum or plasma). Such DNA may be from cells or cell-free DNA. The multiplexed sequential ligation-based analysis methods enrich and/or isolate several or, preferably, many regions of interest in a maternal sample that correspond to individual chromosomes of interest and, in certain aspects, to reference chromosomes that are used to determine the presence or absence of a fetal copy number variation. As described in detail supra, the multiplexed sequential ligation-based analysis methods of the invention employ one or more sequential ligation-based hybridization of regions of interest, and, optionally, separation steps to enhance the content of the regions of interest in the sample. The multiplexed sequential ligation-based analysis methods also provide mechanisms to engineer the copies of the regions of interest for further isolation, amplification or analysis.

The present invention permits analysis of regions of interest on different chromosomes simultaneously and in a preferred embodiment, all of the regions of interest for each sample are amplified in one reaction vessel. In some embodiments, regions of interest from multiple samples are amplified in one reaction vessel, and the sample of origin of the different ligation and amplification products is determined by use of a sample index.

One challenge with the detection of fetal genetic copy number variations or other fetal genetic characteristics in a maternal sample is that the majority of the fetal DNA as a percentage of total DNA in a maternal sample such as maternal blood, serum or plasma may vary from less than one to forty percent, and most commonly is present at or below twenty percent and frequently at or below ten percent. In detecting fetal genetic copy number variations, the relative increase in the extra genetic copy is 50% in the fetal DNA; thus, as a percentage of the total DNA in a maternal sample where, as an example, the fetal DNA is 10% of the total, the increase in the extra genetic copy as a percentage of the total is 5%. If one is to detect such difference robustly through the methods described herein, the variation in the measurement of the extra gene, sequence or chromosome has to be significantly less than the percent increase of the extra chromosome.

In aspects where fetal aneuploidies are evaluated, regions of interest corresponding to multiple loci on a first chromosome are detected and summed to determine the relative frequency of a chromosome in the maternal sample. Next, regions of interest corresponding to multiple loci on a second chromosome are detected and summed to determine the relative frequency of a chromosome in the maternal sample. Frequencies that are higher than expected for one chromosome when compared to the other chromosome in the maternal sample are indicative of a fetal duplication or aneuploidy. The comparison may be between chromosomes that each may be a putative aneuploid in the fetus (e.g., chromosomes 13, 14, 15, 21 and 22), where the likelihood of more than one chromosome being aneuploid is minimal. Alternatively or in addition, the comparison can be between chromosomes where one is putatively aneuploid (e.g., chromosome 13) and the other is very unlikely to be aneuploid (e.g., an autosome such as chromosome 1 or 2), which can act as a reference chromosome. In yet other aspects, the comparison may utilize two or more chromosomes that are putatively aneuploid (i.e., two or more chromosomes selected from chromosomes 13, 14, 15, 18, 21 and 22) only or in addition to one or more reference chromosomes.

In one aspect, the multiplexed sequential ligation-based analysis methods of the invention are used to analyze multiple regions of interest representing selected loci on at least two chromosomes, and the relative frequency of each region of interest from the sample is analyzed to determine a relative chromosome frequency for each chromosome. The chromosomal frequency of the at least two chromosomes is then compared to determine statistically whether a chromosomal abnormality exists.

In another aspect, the multiplexed sequential ligation-based analysis methods of the invention are used to analyze multiple regions of interest representing selected loci on chromosomes of interest, and the relative frequency of each region of interest from the sample is analyzed and independently quantified to determine a relative frequency for each region of interest in the sample. The sums of the regions of interest in the sample are compared to determine statistically whether a chromosomal aneuploidy exists.

In another aspect, subsets of regions of interest on each chromosome are analyzed to determine whether a chromosomal abnormality exists. The frequency for regions of interest can be summed for a particular chromosome, and the summations of the regions of interest used to determine an aneuploidy. This analysis of the sequencing data sums the frequencies of the individual regions of interest from each chromosome and then compares the sum of the regions of interest on one chromosome against another chromosome to determine whether a chromosomal abnormality exists. The subsets of regions of interest can be chosen randomly but with sufficient numbers to yield a statistically significant result in determining whether a chromosomal abnormality exists. Multiple analyses of different subsets of regions of interest can be performed within a maternal sample to yield more statistical power. For example, if there are 100 regions of interest for chromosome 13 and 100 regions of interest for chromosome 21, a series of analyses could be performed that evaluate fewer than 100 regions for each of the chromosomes. In another aspect, specific regions of interest can be selected on each chromosome that are known to have less variation between samples, or by limiting the data used for determination of chromosomal frequency, e.g., by ignoring the data from regions of interest with very high or very low frequency within a sample.

In a particular aspect, the ratio of the frequencies of the regions of interest are compared to a reference mean ratio that has been determined for a statistically significant population of genetically "normal" subjects. In yet another particular aspect, the measured quantity of one or more regions of interest on a chromosome is normalized to account for known variation from sources such as the assay system (e.g., temperature, reagent lot differences), underlying biology of the sample (e.g., nucleic acid content), operator differences, or any other variables.

The data used to determine the frequency of the regions of interest may exclude outlier data that appear to be due to experimental error, or that have elevated or depressed levels based on an idiopathic genetic bias within a particular sample. In one example, the data used for summation may exclude nucleic acid regions with a particularly elevated frequency in one or more samples. In another example, the data used for summation may exclude regions of interest that are found in a particularly low abundance in one or more samples.

The quantity of different regions of interest detectable on certain chromosomes may vary depending upon a number of factors, including general representation of fetal loci in maternal samples, degradation rates of the different nucleic acids representing fetal loci in maternal samples, sample preparation methods, and the like. Thus, in some aspects of the invention the frequencies of the individual regions of interest on each chromosome are summed and then the sum of the regions of interest on one chromosome are compared to the sum of an equal number of regions of interest on another chromosome to determine whether a chromosomal abnormality exists.

The variation between samples and/or for regions of interest within a sample may be minimized using a combination of analytical methods, many of which are described in this application. For instance, variation is lessened by using an internal reference in the assay. An example of an internal reference is the use of a chromosome present in a "normal" abundance (e.g., disomy for an autosome) to compare against the chromosome that may be present in abnormal abundance, i.e., the aneuploidy, in the same sample. While the use of a single such "normal" chromosome as a reference chromosome may be sufficient, it is also possible to use many "normal" chromosomes as the internal reference chromosomes to increase the statistical power of the quantification.

One utilization of an internal reference is to calculate a ratio of abundance of the putatively abnormal chromosomes or sub-chromosomal regions to the abundance of the normal chromosomes or sub-chromosomal regions in a sample, called a chromosomal ratio. In calculating the chromosomal ratio, the abundance or counts of each of the regions of interest for each chromosome or sub-chromosomal region are summed together to calculate the total counts for each chromosome. The total counts for one chromosome are then divided by the total counts for a different chromosome or sub-chromosomal region to create a chromosomal ratio for those two chromosomes or sub-chromosomal regions.

Alternatively, a chromosomal ratio for each chromosome or sub-chromosomal region may be calculated by first summing the counts of each of the regions of interest for each chromosome or sub-chromosomal region, and then dividing the sum for one chromosome or sub-chromosomal region by the total sum for two or more chromosomes. Once calculated, the chromosomal ratio is then compared to the average chromosomal ratio from a normal population.

The average may be the mean, median, mode or other average, with or without normalization and exclusion of outlier data. In a preferred aspect, the mean is used. In developing the data set for the chromosomal ratio from the normal population, the normal variation of the measured chromosomes or sub-chromosomal regions is calculated. This variation may be expressed a number of ways, most typically as the coefficient of variation, or $c_v$. When the chromosomal ratio from the sample is compared to the average chromosomal ratio from a normal population, if the chromosomal ratio for the sample falls statistically outside of the average chromosomal ratio for the normal population, the sample contains an aneuploidy. The criteria for setting the statistical threshold to declare an aneuploidy depend upon the variation in the measurement of the chromosomal ratio and the acceptable false positive and false negative rates for the desired assay. In general, this threshold may be a multiple of the variation observed in the chromosomal ratio. In one example, this threshold is three or more times the variation of the chromosomal ratio. In another example, it is four or more times the variation of the chromosomal ratio. In another example it is five or more times the variation of the chromosomal ratio. In another example it is six or more times the variation of the chromosomal ratio. In the example above, the chromosomal ratio is determined by summing the counts of regions of interest by chromosome or sub-chromosomal region. Typically, the same number of regions of interest for each chromosome or sub-chromosomal region is used. An alternative method for generating the chromosomal ratio would be to calculate the average counts for the regions of interest for each chromosome or chromosomal region. The average may be any estimate of the mean, median or mode, although typically an average is used. The average may be the mean of all counts or some variation such as a trimmed or weighted average. Once the average counts for each chromosome or sub-chromosomal region have been calculated, the average counts for each chromosome or sub-chromosomal region may be divided by the other to obtain a chromosomal ratio between two chromosomes, the average counts for each chromosome may be divided by the sum of the averages for all measured chromosomes to obtain a chromosomal ratio for each chromosome as described above. As highlighted above, the ability to detect a fetal copy number variation in a maternal sample where the fetal DNA is in low relative abundance depends greatly on the variation in the measurements of different regions of interest. Numerous analytical methods can be used that reduce this variation and thus improve the sensitivity of this method to detect aneuploidy.

One method for reducing variability of the assay is to increase the number of regions of interest used to calculate the abundance of the chromosomes or sub-chromosomal regions. In general, if the measured variation of a single region of interest of a chromosome is X % and Y different regions of interest are measured on the same chromosome, the variation of the measurement of the chromosomal abundance calculated by summing or averaging the abundance of each region of interest on that chromosome will be approximately X % divided by $Y^{1/2}$. Stated differently, the variation of the measurement of the chromosome abundance would be approximately the average variation of the measurement of each region of interest's abundance divided by the square root of the number of regions of interest.

In a preferred application of the present invention with respect to fetal copy number variations, the number of regions of interest measured for each chromosome is at least 10. In another preferred aspect of this invention the number of regions of interest measured for each chromosome is at least 24. In yet another preferred aspect of this invention, the number of regions of interest measured for each chromosome is at least 48. In another preferred aspect of this invention, the number of regions of interest measured for each chromosome is at least 100. In another preferred aspect of this invention the number of regions of interest measured for each chromosome is at least 200. There is incremental cost to measuring each region of interest and thus it is important to minimize the number of regions while still generating statistically robust data. In a preferred aspect of this invention, the number of regions of interest measured for each chromosome is less than 2000. In a preferred aspect of this invention, the number of regions of interest measured for each chromosome is less than 1000. In a most preferred aspect of this invention, the number of regions of interest measured for each chromosome is at least 48 and less than 1000. In one aspect, following the measurement of abundance for each region of interest, a subset of the regions of interest may be used to determine the presence or absence of a copy number variation. There are many standard methods for choosing the subset of regions of interest. These methods include outlier exclusion, where the regions of interest with detected levels below and/or above a certain percentile are discarded from the analysis. In one aspect, the percentile may be the lowest and highest 5% as measured by abundance. In another aspect, the percentile may be the lowest and highest 10% as measured by abundance. In another aspect, the percentile may be the lowest and highest 25% as measured by abundance.

Another method for choosing a subset of regions of interest include the elimination of regions that fall outside of some statistical limit. For instance, regions that fall outside of one or more standard deviations of the mean abundance may be removed from the analysis. Another method for choosing the subset of regions of interest may be to compare the relative abundance of a region of interest to the expected abundance of the same region of interest in a healthy population and discard any regions of interest that fail the expectation test. To further minimize the variation in the assay, the number of times each region of interest is measured may be increased. As discussed, in contrast to random methods of detecting fetal copy number variations and other aneuploidies where the genome is measured on average less than once, the methods of the present invention intentionally measure each region of interest multiple times. In general, when counting events, the variation in the counting is determined by Poisson statistics, and the counting variation is typically equal to one divided by the square root of the number of counts. In a preferred aspect of the invention, the regions of interest are each measured on average at least 100 times. In a preferred aspect to the invention, the regions of interest are each measured on average at least 500 times. In a preferred aspect to the invention, the regions of interest are each measured on average at least 1000 times. In a preferred aspect to the invention, the regions of interest are each measured on average at least 2000 times. In a preferred aspect to the invention, the regions of interest are each measured on average at least 5000 times.

In another aspect, subsets of regions of interest can be chosen randomly using sufficient numbers to yield a statistically significant result in determining whether a chromosomal abnormality exists. Multiple analyses of different subsets of regions of interest can be performed within a maternal sample to yield more statistical power. In this example, it may or may not be necessary to remove or eliminate any regions of interest prior to the random analysis. For example, if there are 100 regions of interest for chromosome 13 and 100 regions of interest for chromosome 14, a series of analyses could be performed that evaluate fewer than 100 regions for each of the chromosomes.

Sequence counts also can be normalized by systematically removing sample and assay biases by using median polish on log-transformed counts. A metric can be computed for each sample as the means of counts for a region of interest divided by the sum of the mean of counts for regions of interest on a particular chromosome and the mean of courts for the regions of interest on a different chromosome. A standard Z test of proportions may be used to compute Z statistics:

$$Z_j = \frac{p_j - p_0}{\sqrt{\frac{p_j(1 - p_j)}{n_j}}}$$

where $p_j$ is the observed proportion for a given chromosome of interest in a given sample j, $p_0$ is the expected proportion for the given test chromosome calculated as the median $p_j$, and $n_j$ is the denominator of the proportion metric. Z statistic standardization may be performed using iterative censoring. At each iteration, the samples falling outside of, e.g., three median absolute deviations are removed. After ten iterations, mean and standard deviation were calculated using only the uncensored samples. All samples are then standardized against this mean and standard deviation. The Kolmogorov-Smirnov test (see Conover, Practical Nonparametric Statistics, pp. 295-301 (John Wiley & Sons, New York, N.Y., 1971)) and Shapiro-Wilk's test (see Royston, Applied Statistics, 31:115-124 (1982)) may be used to test for the normality of the normal samples' Z statistics.

In addition to the methods above for reducing variation in the assay, other analytical techniques, many of which are described earlier in this application, may be used in combination. For example, the variation in the assay may be reduced when all of the regions of interest for each sample are interrogated in a single reaction in a single vessel. Similarly, the variation in the assay may be reduced when the universal amplification methods described herein are used. Furthermore, the variation of the assay may be reduced when the number of cycles of amplification is limited.

Determination of Fetal DNA Content in Maternal Sample

Determining the percentage of fetal DNA in a maternal sample may increase the accuracy of the frequency calculations for the regions of interest in a maternal/fetal mixed nucleic acid sample, as knowledge of the fetal contribution provides important information on the expected statistical presence of the regions of interest. Variation from the expectation may be indicative of chromosome copy number. Taking percent fetal into account may be particularly helpful in circumstances where the level of fetal DNA in a maternal sample is low, as the percent fetal contribution can be used to determine the quantitative statistical significance in the variations of levels of regions of interest in a maternal sample.

In some specific aspects, the relative maternal contribution of maternal DNA at an allele of interest can be compared to the non-maternal contribution at that allele to determine approximate fetal DNA concentration in the sample. In other specific aspects, the relative quantity of solely paternally-derived sequences (e.g., Y-chromosome sequences or paternally-specific polymorphisms) can be used to determine the relative concentration of fetal DNA in a maternal sample. Another exemplary approach to determining the percent fetal contribution in a maternal sample is through the analysis of DNA fragments with different patterns of DNA methylation between fetal and maternal DNA.

In circumstances where the fetus is male, percent fetal DNA in a sample can be determined through detection of Y-specific nucleic acids and comparison to calculated maternal DNA content. Quantities of an amplified Y-specific nucleic acid, such as a region from the sex-determining region Y gene (SRY), which is located on the Y chromosome and is thus representative of fetal DNA, can be determined from the sample and compared to one or more amplified genes that are present in both maternal DNA and fetal DNA and that are preferably not from a chromosome believed to potentially be aneuploid in the fetus, e.g., an autosomal region that is not on chromosome 13, 14, 15, 18, 21, or 22.

In some circumstances such as with a female fetus, the determination of fetal polymorphisms requires targeted SNP and/or mutation analysis to identify the presence of fetal DNA in a maternal sample. In some aspects, the use of prior genotyping of the father and mother can be performed. For example, the parents may have undergone such genotype determination for identification of disease markers, e.g., determination of the genotype for disorders such as cystic fibrosis, muscular dystrophy, spinal muscular atrophy or even the status of the RhD gene may be determined. Such difference in polymorphisms, copy number variants or mutations can be used to determine the percentage fetal contribution in a maternal sample.

In an alternative preferred aspect, the percent fetal cell free DNA in a maternal sample can be quantified using multiplexed SNP detection without using prior knowledge of the maternal or paternal genotype. In this aspect, two or more polymorphic regions of interest with a known SNP in each region are used. In a preferred aspect, the selected polymorphic nucleic acid regions are located on an autosomal chromosome that is unlikely to be aneuploid, e.g., Chromosome 6.

In a preferred embodiment, the selected polymorphic nucleic acid regions are amplified in one reaction in one vessel. Each allele of the selected polymorphic nucleic acid regions in the maternal sample is identified and quantified using high throughput sequencing. As described previously, polymorphisms may be identified using differentially-sequenced oligonucleotide probe sets or by using non-differentially-sequenced probe sets and relying on sequencing to identify the polymorphisms. Following sequence determination, loci are identified where the maternal and fetal genotypes are different, e.g., the maternal genotype is homozygous and the fetal genotype is heterozygous. This identification is accomplished by observing a high relative frequency of one allele (>60%) and a low relative frequency (<20% and >0.15%) of the other allele for a particular region of interest. The use of multiple loci is particularly advantageous as it reduces the amount of variation in the measurement of the abundance of the alleles. All or a subset of the loci that meet this requirement are used to determine fetal concentration through statistical analysis.

In one aspect, fetal concentration is determined by summing the low frequency alleles from two or more loci together, dividing by the sum of the high and low frequency alleles and multiplying by two. In another aspect, the percent fetal cell free DNA is determined by averaging the low frequency alleles from two or more loci, dividing by the average of the high and low frequency alleles and multiplying by two.

For many alleles, maternal and fetal sequences may be homozygous and identical, and as this information does not distinguish between maternal and fetal DNA, it is not useful in the determination of percent fetal DNA in a maternal sample. Instead, allelic information where there is a difference between the fetal and maternal DNA (e.g., a fetal allele containing at least one allele that differs from the maternal allele) is utilized in calculations of percent fetal. Data pertaining to allelic regions that are the same for the maternal and fetal DNA are thus not selected for analysis or are removed from the pertinent data prior to determination of percentage fetal DNA so as not to swamp out the useful data. Exemplary methods for quantifying fetal DNA in maternal plasma can be found, e.g., in Chu et al., Prenat Diagn, 30:1226-29 (2010), which is incorporated herein by reference.

In one aspect, regions of interest may be excluded if the amount or frequency of the region appears to be an outlier due to experimental error, or from idiopathic genetic bias within a particular sample. In another aspect, regions of interest may undergo statistical or mathematical adjustment such as normalization, standardization, clustering, or transformation prior to summation or averaging. In another aspect, regions of interest may undergo both normalization and data experimental error exclusion prior to summation or averaging. In a preferred aspect, 12 or more loci are used for the analysis. In another preferred aspect, 24 or more loci are used for the analysis. In another preferred aspect, 48 or more loci are used for the analysis. In another aspect, one or more indices are used to identify the sample, the locus, the allele or the identification of the region of interest.

In one preferred aspect, the percentage fetal contribution in a maternal sample can be quantified using tandem SNP detection in the maternal and fetal alleles. Techniques for identifying tandem SNPs in DNA extracted from a maternal sample are disclosed in Mitchell et al, U.S. Pat. Nos. 7,799,531 and 8,399,195 and U.S. Ser. Nos. 12/689,924 and 13/714,242. These references describe the differentiation of fetal and maternal loci through detection of at least one tandem single nucleotide polymorphism (SNP) in a maternal sample that has a different haplotype between the fetal and maternal genome. Identification and quantification of these haplotypes can be performed directly on the maternal sample, as described in the Mitchell et al. disclosures, and used to determine the percent fetal contribution in the maternal sample.

Use of Percent Fetal Cell Free DNA to Optimize Fetal Aneuploidy Detection

Once percent fetal cell free DNA has been calculated, this data may be combined with methods for aneuploidy detection to determine the likelihood that a fetus may contain an aneuploidy. In one preferred aspect, the chromosomal ratio and its variation for the normal population are determined from normal samples that have a similar percentage of fetal DNA. An expected aneuploid chromosomal ratio for a DNA sample with that percent fetal cell free DNA is calculated by adding the percent contribution from the aneuploid chromosome. The chromosomal ratio for the sample may then be compared to the chromosomal ratio for the normal population and to the expected aneuploid chromosomal ratio to determine statistically, using the variation of the chromosomal ratio, if the sample is more likely normal or aneuploid, and the statistical probability that it is one or the other.

In a preferred aspect, the selected regions of a maternal sample include both regions for determination of fetal DNA content as well as non-polymorphic regions from two or more chromosomes to detect a copy number variation in a single reaction. The single reaction helps to minimize the risk of contamination or bias that may be introduced during various steps in the assay system which may otherwise skew results when utilizing fetal DNA content to help determine the presence or absence of a chromosomal abnormality.

In other aspects, a region of interest or regions of interest may be utilized both for determination of fetal DNA content as well as detection of fetal chromosomal abnormalities. The alleles for regions of interest can be used to determine fetal DNA content and these same regions of interest can then be used to detect fetal chromosomal abnormalities ignoring the allelic information. Utilizing the same regions of interest for both fetal DNA content and detection of chromosomal abnormalities may further help minimize any bias due to experimental error or contamination.

In one embodiment, fetal source contribution in a maternal sample regardless of fetal gender is measured using autosomal SNPs (see, Sparks, et al., Am. J. Obstet & Gyn., 206: 319.e1-9 (2012)). The processes utilized do not require prior knowledge of paternal genotype, as the non-maternal alleles are identified during the methods without regard to knowledge of paternal inheritance. A maximum likelihood estimate using the binomial distribution may be used to calculate the estimated fetal nucleic acid contribution across several informative loci in each maternal sample. The processes for calculation of fetal acid contribution used are described, for example, in U.S. Ser. No. 13/553,012, filed 9 Jul. 2012, which is incorporated by reference. The polymorphic regions used for determination of fetal contribution may be from chromosomes 1-12, and preferably do not target the blood group antigens. The estimate of fetal contribution from the polymorphic assays is used to define expected response magnitudes when a test chromosome is trisomic, which informs the statistical testing. The test statistic may consist of two components: a measure of deviation from the expected proportion when the sample is disomic; and a measure of deviation from the expected proportion when the sample is trisomic. Each component is in the form of a Wald statistic (e.g., Harrell, Regression modeling strategies, (2001, Springer-Verlag), Sections 9.2.2 and 10.5) which compares an observed proportion to an expected proportion and divides by the variation of the observation.

The statistic Wj may be used to measure the deviation from expectation when the sample j is disomic, and is defined as $$W_j = \frac{p_j - p_0}{\sigma_{p_j}},$$

where $p_j$ and $p_0$ are defined as described supra with the Z statistic, and $\sigma_{p_j}$ is the standard deviation of the observed proportion of representation for a given chromosome of interest. The standard deviation may be estimated using parametric bootstrap sampling to create a distribution of $p_j$ proportions based on the mean counts and standard errors for our chromosomes of interest. The second statistic is $\hat{W}_j$, which replaces $p_0$ with the fetal fraction adjusted reference proportion $\hat{p}_j$ is defined as $$\hat{p}_j = \frac{(1 + 0.5 f_j)p_0}{((1 + 0.5 f_j)p_0)(1 - p_0)},$$

where $f_j$ is the fetal fraction for sample j and $p_0$ is the reference proportion as before. This adjustment accounts for the increased representation of a test chromosome when the fetus was trisomic. Because this variance of counts across many loci is measured as a natural result of using multiple non-polymorphic assays for the test chromosomes, all estimates are taken within a nascent data set and do not require external reference samples or historical information with normalizing adjustments to control for process drift as is typically required for variance around the expected proportion.

The final statistic used was $S_j = W_j + \hat{W}_j$. Conceptually, deviations from disomic expectation and trisomic expectation are simultaneously evaluated and summarized into this single statistic. The particular advantage of combining these two indicators is that while deviation from disomy might be high, it may not reach the deviation expected for trisomy at a particular fetal contribution level. The $\hat{W}_j$ component will be negative in this case, in effect penalizing the deviation from disomy. An $S_j=0$ indicated an equal chance of being disomic vs. trisomic.

Detection of Other Agents or Risk Factors in Mixed Sample

Given the multiplexed nature of the enrichment methods of the invention, in certain aspects it may be beneficial to utilize the methods to detect other nucleic acids that may be present in very small quantities in a sample—i.e., rare nucleic acids-that could pose a risk to the health of an individual or otherwise impact on clinical decisions about the treatment or prognostic outcome for an individual. Detection of exogenous agents in a mixed sample may be indicative of exposure to and infection by an infectious agent, and this finding have an impact on patient care or management of an infectious disease. Thus, the methods of the invention may be used to identify exogenous nucleic acids associated with active or latent infections; somatic mutations or copy number variations associated with autoimmune disorders or malignancies (e.g., breast cancer), or any other health issue that may impact an individual.

In one example, changes in immunity and physiology during pregnancy may make pregnant women more susceptible to or more severely affected by infectious diseases. In fact, pregnancy itself may be a risk factor for acquiring certain infectious diseases, such as toxoplasmosis, Hansen disease, and listeriosis. In addition, for pregnant women or subjects with suppressed immune systems, certain infectious diseases such as influenza and varicella may have a more severe clinical course, increased complication rate, and higher case-fatality rate. Identification of infectious disease agents may therefore allow better treatment for maternal disease during pregnancy, leading to a better overall outcome for both mother and fetus. In addition, certain infectious agents can be passed to the fetus via vertical transmission, i.e. spread of infections from mother to baby. These infections may occur while the fetus is still in the uterus, during labor and delivery, or after delivery (such as while breastfeeding). Exemplary infections that can be spread via vertical transmission, and which can be tested for using the assay methods of the invention, include but are not limited to congenital infections, perinatal infections and postnatal infections. Congenital infections are passed in utero by crossing the placenta to infect the fetus. Many infectious microbes can cause congenital infections, leading to problems in fetal development or even death. TORCH is an acronym for several of the more common congenital infections. These are: toxoplasmosis, other infections (e.g., syphilis, hepatitis B, Coxsackie virus, Epstein-Barr virus, varicella-zoster virus (chicken pox), and human parvovirus B19 (fifth disease)), rubella, cytomegalovirus (CMV), and herpes simplex virus. Perinatal infections refer to infections that occur as the baby moves through an infected birth canal or through contamination with fecal matter during delivery. These infections can include, but are not limited to, sexually-transmitted diseases (e.g., gonorrhea, chlamydia, herpes simplex virus, human papilloma virus, etc.) CMV, and Group B Streptococci (GBS).

Thus, in some preferred aspects, the enrichment methods of the invention may include detection of exogenous sequences, e.g., sequences from infectious organisms that may have an adverse effect on the health and/or viability of an individual.

EXAMPLES

Example 1

Multiplexed Linear Replication (MLR) of DNA Loci

15 µl (7.5 ng) of DNA was added to each well of a 96-well plate and 30 µl of an amplification mix (5× Phusion HF buffer (Finnzymes, Espoo, Finland), 5M betaine, 25 mM dNTPs, 2.0 µM biotinylated primer and 2 units Phusion polymerase ((Finnzymes, Espoo, Finland)) was added to each well. The plate was sealed with an adhesive plate sealer, shaken at 1500 rpm for 1 min then spun for 10 seconds at 250×g using a centrifuge. Standard PCR was carried out using cycles of 95° C. for 2 minutes and 61° C. for 2 minutes.

After thermocycling was complete, the DNA was isolated from each sample, and resuspended in 30 µl TE buffer. Individual DNA isolates were transferred to a new 96-well plate.

Example 2

First Round of Multiplexed Ligation-Based Analysis 10 mg of magnetic streptavidin beads (Invitrogen, Carlsbad, Calif.) was dispensed into a 15 ml conical tube and placed on a 15 ml magnetic stand. Once the streptavidin beads cleared, the supernatant was discarded. 6 ml of binding buffer (100 mM Tris pH 8.0, 10 mM $Na_2$ EDTA, 500 mM NaCl, 58% formamide, 3.33 ng/µl yeast RNA carrier stock (Ambion, Grand Island, N.Y.) and 0.17% TWEEN™ 80) was then dispensed into the tube and 1 µg/µl per reaction of streptavidin beads were resuspended by vortexing. 1 ml of 40 nM primer pool was transferred into the 15 ml conical tube containing the 6 ml binding buffer and the tube was vortexed again.

70 µl the solution was dispensed into each well of the 96-well plate containing the eluate. The annealing reaction comprised: 1000 mM Tris pH 8.0, 500 mM $Na_2$EDTA, 5000 mM $NaCl_2$, 100% formamide, 1000.0 ng/µl yeast carrier stock, 10% TWEEN™ 80, and 40 nM of the primer pool. The 96-well plate was sealed with an adhesive plate sealer and mixed using a shaker, 1200 rpm for 1 minute. Standard PCR was carried out using cycles of 70° C. for 5 minutes, and 30° C. for 3 minutes each. The plate was spun for 10 seconds at 250×g and placed on a raised-bar magnetic plate, where the beads were allowed to clear the solution. The supernatant was then discarded. The beads were washed with buffer, the plate was shaken for 1 minute at 1900 rpm, and placed on a raised-bar magnetic plate where the beads were allowed to clear the solution. This wash process was repeated.

The 96-well plate was removed from the raised-bar magnetic plate after the last wash, and 50 µl wash buffer (1000 mM Tris pH 8.0, 500 mM $Na_2$EDTA, 5000 mM $NaCl_2$, 1000 ng/µl yeast RNA carrier stock (Ambion, Grand Island, N.Y.), 10% TWEEN™ 80, and molecular $H_2O$) was added to each well. The wells were mixed by placing the plate on a shaker for 1 minute at 1900 rpm and the plate placed on a raised-bar magnetic plate. Once the streptavidin beads cleared solution, the supernatant was removed and discarded and the wash step was repeated.

20 µl of TE buffer was then added to each well, the plate was sealed with an adhesive plate sealer and the plate was shaken for 1 minute at 1900 rpm. The plate was placed at 95° C. for 1 minute. The plate was then spun for 10 seconds at 250×g and placed on a raised-bar magnetic plate, where the beads were allowed to clear the solution. 25 µl supernatant was aspirated from each well and dispensed into a fresh 96-well plate.

15 µl of PCR reaction mix (final concentration: 5 M betaine, 5× Phusion HF buffer (Finnzymes, Espoo, Finland), 0.5 µM primers, 25 mM dNTPs, 10% TWEEN™ 80, and 2 units Phusion HS DNA polymerase II (Finnzymes, Espoo, Finland)) was dispensed into each well, and the plate was shaken for 1 minute at 1500 rpm. Standard PCR was carried out using cycles of 95° C. for 1 minute, 68° C. for 2 minutes, 70° C. for 0.5 minutes, followed by a 5 minute extension at 70° C. 10% of the PCR product was run on a 3% TBE agarose gel.

Example 3

Second Round of Multiplexed Ligation-Based Analysis 10 mg magnetic straptavidin beads were dispensed into a 15 ml comical tube and placed on a magnetic stand and the solution allowed to clear. The supernatant was removed and the beads were then resuspended in 6 ml of binding buffer (100 mM Tris pH 8.0, 10 mM Na2 EDTA, 500 mM NaCl, 58% formamide, 3.33 ng/µl yeast RNA carrier stock (Ambion, Grand Island, N.Y.) and 0.17% TWEEN™ 80) was then dispensed into the tube and the magnetic streptavidin beads were resuspended by vortexing. 1 ml of 40 nM primer pool was transferred into the 15 ml conical tube containing the 6 ml binding buffer and the tube was vortexed again. 70 µl of the solution was dispensed into each well of the 96-well plate containing the eluate. The annealing reaction comprised: 1000 mM Tris pH 8.0, 500 mM $Na_2$ EDTA, 5000 mM $NaCl_2$, 100% formamide, 1000 ng/µl yeast carrier stock, 10% TWEEN™-80, and 30 µM of the primer pool. The 96-well plate was sealed with an adhesive plate sealer and mixed using a shaker, 1200 for 1 minute.

The solution was placed at 70° C. for 5 minutes and 30° C. for 3 minutes each.

The plate was spun for 10 seconds at 250×g and placed on a raised-bar magnetic plate, where the beads were allowed to clear the solution. The supernatant was discarded. The beads were washed with buffer (dilute binding buffer), the plate was shaken for 1 minutes at 1900 rpm, and placed on a raised-bar magnetic plate where the beads were allowed to clear the solution. This wash process was repeated. The 96-well plate was removed from the raised-bar magnetic plate after the last wash, and 37 µl ligation mix (10× Taq polymerase buffer (Enzymatics, Beverly, Mass.), 1000 ng/µl yeast RNA carrier stock (Ambion, Grand Island, N.Y.), 10% TWEEN™-80, and 40 units/µl Taq ligase (Enzymatics, Beverly, Mass.)) was added to each well. The wells were mixed by placing the plate on a shaker for 1 minute at 1900 rpm, and the plate was placed on a raised-bar magnetic plate and the solution wash allowed to clear and the supernatant removed. This wash was repeated. The solution was placed at 45° C. The plate was spun for 10s at 250×g and placed on a raised-bar magnetic plate.

Once the streptavidin beads cleared solution, the supernatant was removed and discarded, 50 µl buffer (1000 mM Tris pH 8.0, 500 mM $Na_2$ EDTA, 5000 mM $NaCl_2$, 1000 ng/µl yeast RNA carrier stock and 10% TWEEN™-80) was added to each well and the plate was shaken for 1 minute at 1900 rpm. Again, the plate was placed on a raised-bar magnetic plate, the beads were allowed to clear the solution and the supernatant was removed and discarded. The was was repeated. 30 µl of TE buffer was then added to each well, the plate was sealed with an adhesive plate sealer and the plate was shaken for 1 minute at 1900 rpm. The solution was placed at 95° C. for 1 minute. The plate was then spun for 10 seconds at 250×g and placed on a raised-bar magnetic plate, where the beads were allowed to clear the solution.

25 μl was aspirated from each well and dispensed into a fresh 96-well plate. 21 μl of PCR reaction mix (final concentration: 5 M betaine, 5× PHUSION™ HF buffer (Finnzymes, Espoo, Finland), 0.5 μM primers, 25 mM dNTPs, 10% TWEEN™-80, and 2 units PHUSION™ HF DNA polymerase II (Finnzymes, Espoo, Finland)) was dispensed into each well, and the plate was shaken for 1 minute at 1500 rpm. Standard PCR was carried out using cycles of 95° C. for 0.5 minute, 68° C. for 2 minutes, 70° C. for 0.5 minutes, followed by a 5 minute extension at 70° C. A portion of the sample was visualized on a 3% TBE agarose gel and the rest of the sample was prepared for sequencing.

Example 4

Results 1

An experiment performed for the first replication reaction, as described in Example 1, using differing genome equivalents of input DNA and using differing concentrations of primer resulted in generally at least >95% and more typically >98% of sequencing reads that mapped back to the input DNA (88 out of 104 samples).

Example 5

Results 2

Additional experiments were performed in which three investigations were conducted using the methods described herein to determine the detection rate of S. cerevisiae in the presence of varying amounts of human and E. Coli gDNA. In a first experiment, 3000 genomes of S. cerevisiae were investigated in the presence of 3000 genomes of human and E. Coli gDNA. In this experiment, the detection rate of S. cerevisiae was 99.93%. In a second experiment, 30 genomes of S. cerevisiae were investigated in the 3000 genomes of human gDNA and 3000 genomes of E. Coli gDNA. In this experiment, the detection rate of S. cerevisiae was 99.27%. In a third experiment, 30 genomes of S. cerevisiae were investigated in the presence of 0 genomes of E. Coli and 3000 genomes of human gDNA. In this investigation, the detection rate of S. cerevisiae was 99.68%.

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §112, ¶6.

We claim:

1. A method for identifying a genomic region of interest from a single source in a sample comprising DNA from two different sources, comprising the steps of:

providing a sample comprising DNA from two different sources;

introducing to the sample a first set of oligonucleotide probes comprising a first fixed sequence oligonucleotide complementary to a 3' region in a genomic region of interest, a second fixed sequence oligonucleotide complementary to a 5' region in the genomic region of interest, and one or more bridging oligonucleotides that hybridize to the genomic region of interest between and adjacent to the first and second fixed sequence oligonucleotides of the first set of oligonucleotide probes;

hybridizing the first set of oligonucleotide probes to the genomic region of interest in the sample;

ligating the hybridized oligonucleotides of the first set of oligonucleotide probes to create first ligation products complementary to the genomic region of interest;

introducing to the first ligation products a second set of oligonucleotide probes comprising a first fixed sequence oligonucleotide complementary to a 3' region in the first ligation product, a second fixed sequence oligonucleotide complementary to a 5' region in the first ligation product, and one or more bridging oligonucleotides that hybridize to the first ligation product between and adjacent to the first and second fixed sequence oligonucleotides of the second set of oligonucleotide probes;

hybridizing the second set of oligonucleotide probes to the first ligation products;

ligating the hybridized oligonucleotides of the second set to create second ligation products complementary to the first ligation products;

amplifying the second ligation products to create amplification products; and analyzing the amplification products, wherein analysis of the amplification products identifies the genomic region of interest from the single source in the sample.

2. The method of claim 1, wherein at least one fixed sequence oligonucleotide of the second set of oligonucleotide probes comprises a complementary region that overlaps a ligation junction of the first ligation products.

3. The method of claim 1, wherein both the first and second fixed sequence oligonucleotides of the second set of oligonucleotide probes comprise a complementary region that overlaps a ligation junction of the first ligation products.

4. The method of claim 1, wherein at least one fixed sequence oligonucleotide of the second set of oligonucleotide probes comprises a region that is complementary to the genomic region of interest.

5. The method of claim 1, wherein both fixed sequence oligonucleotides of the second set of oligonucleotide probes comprise a region that is complementary to the genomic region of interest.

6. The method of claim 1, further comprising a step of amplifying the first ligation products after the first ligating step and before the second introducing step.

7. The method of claim 6, wherein the amplification is linear.

8. The method of claim 6, wherein the amplification is exponential.

9. The method of claim 1, wherein the method is performed for two or more genomic regions of interest from the single source.

10. The method of claim 9, wherein at least 24 different regions of interest are interrogated.

11. The method of claim 10, wherein at least 46 different regions of interest are interrogated.

12. The method of claim 11, wherein at least 92 different regions of interest are interrogated.

13. The method of claim 1, wherein the first and/or second sets of oligonucleotide probes comprise more than one bridging oligonucleotide.

14. The method of claim 1, wherein the first and second sets of oligonucleotide probes comprise a single bridging oligonucleotide.

15. The method of claim 1, wherein the amplification of the second ligation products is linear.

16. The method of claim 1, wherein the amplification of the second ligation products is exponential.

17. A method for identifying a genomic region of interest from a single source in a sample comprising DNA from two different sources, comprising the steps of:
  providing a sample comprising DNA from two different sources;
  introducing to the sample a first set of oligonucleotide probes comprising a first fixed sequence oligonucleotide complementary to a 3' region in a genomic region of interest and a second fixed sequence oligonucleotide complementary to a 5' region in the genomic region of interest, wherein the first and second fixed sequence oligonucleotides are complementary to non-adjacent regions in the genomic region of interest;
  hybridizing the first set of oligonucleotide probes to the genomic region of interest in the sample;
  extending the region between the first fixed sequence oligonucleotide and the second fixed sequence oligonucleotide of the first set of oligonucleotide probes with a polymerase and dNTPs to create contiguously hybridized oligonucleotides of the first set of oligonucleotide probes complementary to the genomic region of interest;
  ligating the contiguously hybridized oligonucleotides of the first set to of oligonucleotide probes create first ligation products complementary to the genomic region of interest;
  introducing to the first ligation products a second set of oligonucleotide probes comprising a first fixed sequence oligonucleotide complementary to a 3' region in the first ligation product and a second fixed sequence oligonucleotide complementary to a 5' region in the first ligation product, wherein the first and second fixed sequence oligonucleotides are complementary to non-adjacent regions in the first ligation product;
  hybridizing the second set of oligonucleotide probes to the first ligation products;
  extending the region between the first fixed sequence oligonucleotide and the second fixed sequence oligonucleotide of the second set with a polymerase and dNTPs to create contiguously hybridized oligonucleotides of the second set of oligonucleotide probes complementary to the first ligation product;
  ligating the contiguously hybridized oligonucleotides of the second set of oligonucleotide probes to create second ligation products complementary to the first ligation products;
  amplifying the second ligation products to create amplification products; and
  analyzing the amplification products, wherein the analysis of the amplification products identifies the genomic region of interest from the single source in the sample.

18. The method of claim 17, wherein at least one fixed sequence oligonucleotide of the second set of oligonucleotide probes comprises a complementary region that overlaps a ligation junction of the first ligation products.

19. The method of claim 17, wherein both the first and second fixed sequence oligonucleotides of the second set of oligonucleotide probes comprise a complementary region that overlaps with a ligation junction of the first ligation products.

20. The method of claim 17, wherein at least one fixed sequence oligonucleotide of the second set of oligonucleotide probes comprises a region that is complementary to the genomic region of interest.

21. The method of claim 17, wherein both fixed sequence oligonucleotides of the second set of oligonucleotide probes comprise a region that is complementary to the genomic region of interest.

22. The method of claim 17, further comprising a step of amplifying the first ligation products after the first ligating step and before the second introducing step.

23. The method of claim 22, wherein the amplification is linear.

24. The method of claim 22, wherein the amplification is exponential.

25. The method of claim 17, wherein the method is performed for two or more genomic regions of interest from the single source.

26. The method of claim 25, wherein at least 24 different regions of interest are interrogated.

27. The method of claim 26, wherein at least 46 different regions of interest are interrogated.

28. The method of claim 27, wherein at least 92 different regions of interest are interrogated.

29. The method of claim 28, wherein at least 180 different regions of interest are interrogated.

30. The method of claim 29, wherein at least 360 different regions of interest are interrogated.

31. The method of claim 17, wherein the amplification of the second ligation products is linear.

32. The method of claim 17, wherein the amplification of the second ligation products is exponential.

33. A method for identifying a genomic region of interest from a single source in a sample comprising DNA from two different sources, comprising the steps of:
  providing a sample comprising DNA from two different sources;
  introducing to the sample a first set of oligonucleotide probes comprising a first fixed sequence oligonucleotide complementary to a 3' region in a genomic region of interest and a second fixed sequence oligonucleotide complementary to a 5' region in the genomic region of interest;
  hybridizing the first set of oligonucleotide probes to the genomic region of interest in the sample;
  ligating the hybridized oligonucleotides of the first set of oligonucleotide probes to create first ligation products complementary to the genomic region of interest;
  introducing to the first ligation products a second set of oligonucleotide probes comprising a first fixed sequence oligonucleotide complementary to a 3' region in the first ligation product and a second fixed sequence oligonucleotide complementary to a 5' region in the first ligation product;
  hybridizing the second set of oligonucleotide probes to the first ligation products;
  ligating the hybridized oligonucleotides of the second set of oligonucleotide probes to create second ligation products complementary to the first ligation products;
  amplifying the second ligation products to create amplification products; and
  analyzing the amplification products, wherein the analysis of the amplification products identifies the genomic region of interest from the single source in the sample.

34. The method of claim 33, wherein the first set of oligonucleotide probes further comprises one or more bridging oligonucleotides that hybridize to the genomic region of interest between and adjacent to the first and second fixed sequence oligonucleotides of the first set of oligonucleotide probes.

35. The method of claim 33, wherein the second set further comprises one or more bridging oligonucleotides that hybridize to the first ligation products between and adjacent to the first and second fixed sequence oligonucleotides of the second set of oligonucleotide probes.

36. The method of claim 33, wherein the oligonucleotides of the first set of oligonucleotide probes are complementary to non-adjacent regions in the genomic region of interest, and wherein the region between the first fixed sequence oligonucleotide and the second fixed sequence oligonucleotide of the first set is extended with a polymerase and dNTPs to create contiguously complementary oligonucleotides of the first set.

37. The method of claim 33, wherein the oligonucleotides of the second set of oligonucleotide probes are complementary to non-adjacent regions in the first ligation products, and wherein the region between the first fixed sequence oligonucleotide and the second fixed sequence oligonucleotide of the second set is extended with a polymerase and dNTPs to create contiguously complementary oligonucleotides of the second set.

38. The method of claim 33, wherein the fixed sequence oligonucleotides of the first set of oligonucleotide probes are complementary to adjacent regions in the genomic region of interest.

39. The method of claim 33, wherein the fixed sequence oligonucleotides of the second set of oligonucleotide probes are complementary to adjacent regions in the first ligation products.

40. The method of claim 33, wherein at least one fixed sequence oligonucleotide of the second set of oligonucleotide probes comprises a complementary region that overlaps a ligation junction of the first ligation products.

41. The method of claim 33, wherein both the first and second fixed sequence oligonucleotides of the second set of oligonucleotide probes comprise a complementary region that overlaps with a ligation junction of the first ligation products.

42. The method of claim 33, wherein at least one fixed sequence oligonucleotide of the second set of oligonucleotide probes comprises the region of a fixed sequence oligonucleotide of the first set of oligonucleotide probes that is complementary to the genomic region of interest.

43. The method of claim 33, wherein both fixed sequence oligonucleotides of the second set of oligonucleotide probes comprise a region of the fixed sequence oligonucleotides that is complementary to the genomic region of interest.

44. The method of claim 33, further comprising a step of amplifying the first ligation products after the first ligating step and before the second introducing step.

45. The method of claim 44, wherein the amplification is linear.

46. The method of claim 44, wherein the amplification is exponential.

47. The method of claim 33, wherein the method is performed for two or more genomic regions of interest from the single source.

48. The method of claim 47, wherein at least 24 different regions of interest are interrogated.

49. The method of claim 48, wherein at least 46 different regions of interest are interrogated.

50. The method of claim 49, wherein at least 92 different regions of interest are interrogated.

51. The method of claim 33, wherein the first and/or second sets of oligonucleotide probes comprise more than one bridging oligonucleotide.

52. The method of claim 33, wherein the first and second sets of oligonucleotide probes comprise a single bridging oligonucleotide.

53. The method of claim 33, wherein the amplification of the second ligation products is linear.

54. The method of claim 33, wherein the amplification of the second ligation products is exponential.

* * * * *